United States Patent
Yoshida et al.

(10) Patent No.: US 9,453,790 B2
(45) Date of Patent: Sep. 27, 2016

(54) BLOOD ANALYZER, BLOOD ANALYZING METHOD, AND COMPUTER PROGRAM PRODUCT

(75) Inventors: Ayumu Yoshida, Kobe (JP); Shinichiro Oguni, Kobe (JP); Tatsuya Narikawa, Kobe (JP); Saori Suzuki, Kobe (JP)

(73) Assignee: SYSMEX CORPORATION, Kobe (JP)

(*) Notice: Subject to any disclaimer, the term of this patent is extended or adjusted under 35 U.S.C. 154(b) by 699 days.

(21) Appl. No.: 12/729,989

(22) Filed: Mar. 23, 2010

(65) Prior Publication Data

US 2010/0248300 A1    Sep. 30, 2010

(30) Foreign Application Priority Data

Mar. 26, 2009  (JP) .................. 2009-076019
Dec. 25, 2009  (JP) .................. 2009-294442

(51) Int. Cl.
| | |
|---|---|
| *G01N 15/06* | (2006.01) |
| *G01N 33/00* | (2006.01) |
| *G01N 27/00* | (2006.01) |
| *G01N 21/00* | (2006.01) |
| *G01N 15/14* | (2006.01) |
| *G01N 15/10* | (2006.01) |

(52) U.S. Cl.
CPC ... *G01N 15/1459* (2013.01); *G01N 2015/1006* (2013.01); *G01N 2015/1402* (2013.01)

(58) Field of Classification Search
CPC ............. G01N 15/14; G01N 15/1459; G01N 2015/008; G01N 2015/1486; G01N 33/80; C12M 1/3476
USPC ............... 422/73, 68.1, 82.01, 82.05; 436/10
See application file for complete search history.

(56) References Cited

U.S. PATENT DOCUMENTS

| | | | | |
|---|---|---|---|---|
| 5,939,326 A * | 8/1999 | Chupp et al. | | 436/43 |
| 5,958,776 A * | 9/1999 | Sakata | ... | G01N 33/5094 435/29 |
| 6,004,816 A | 12/1999 | Mizukami et al. | | |
| 6,197,593 B1 * | 3/2001 | Deka et al. | | 436/63 |
| 6,228,652 B1 * | 5/2001 | Rodriguez et al. | | 436/63 |
| 6,444,471 B1 * | 9/2002 | Johnson | ... | G01N 33/49 252/408.1 |
| 7,488,574 B2 * | 2/2009 | Oguni | | 435/4 |
| 7,633,604 B2 * | 12/2009 | Ikeuchi et al. | | 356/39 |
| 7,892,841 B2 * | 2/2011 | Tsuji et al. | | 436/63 |
| 7,892,850 B2 * | 2/2011 | Oguni et al. | | 436/172 |
| 2002/0086344 A1 * | 7/2002 | Tsuji | ... | G01N 33/5002 435/29 |
| 2003/0219850 A1 * | 11/2003 | Tsuji | ... | G01N 1/30 435/40.5 |
| 2005/0002826 A1 * | 1/2005 | Oguni | ... | G01N 33/5094 422/73 |

(Continued)

*Primary Examiner* — Dean Kwak
(74) *Attorney, Agent, or Firm* — Brinks Gilson & Lione

(57) ABSTRACT

A blood analyzer comprising: a specimen preparation section for preparing a measurement specimen that is used to measure a white blood cell count among CBC measurement items; a measurement section for obtaining optical information from blood cells contained in the measurement specimen; and a controller carrying out operations comprising: classifying blood cells contained in the measurement specimen into at least white blood cells and blood cells suspected to be abnormal blood cells based on the optical information; obtaining distribution data of the white blood cells and distribution data of the blood cells suspected to be abnormal blood cells; counting the white blood cells based on the distribution data of the white blood cells; and determining presence or absence of the abnormal blood cells in the blood sample, based on the distribution data of the blood cells suspected to be abnormal blood cells. A blood analyzing method and a computer program product are also disclosed.

15 Claims, 11 Drawing Sheets

(56) References Cited

U.S. PATENT DOCUMENTS

| | | | |
|---|---|---|---|
| 2005/0272026 A1* | 12/2005 | Oguni | 435/4 |
| 2006/0223138 A1* | 10/2006 | Mori | G01N 15/147 435/40.5 |
| 2007/0020721 A1* | 1/2007 | Yoshida et al. | 435/34 |
| 2007/0231913 A1* | 10/2007 | Tsuji | G01N 15/1459 436/63 |
| 2008/0102526 A1 | 5/2008 | Mori et al. | |
| 2008/0187951 A1* | 8/2008 | Nagai | G01N 15/12 435/29 |
| 2008/0187990 A1 | 8/2008 | Nagai et al. | |
| 2009/0076736 A1* | 3/2009 | Ikeuchi et al. | 702/21 |

* cited by examiner

| GENERAL FORMULA | DYE NAME | STRUCTURE ||||| 
| | | R1 | R2 | R3 | R4 | X |
|---|---|---|---|---|---|---|
|  | NK-529 | CH₃ | CH₃ | H | H | I⁻ |
| | NK-2670 | CH₃ | CH₃ | H | H | ClO₄⁻ |
| | NK-3750 | CH₃ | CH₃ | H | H | BF₄⁻ |
| | NK-3383 | C₄H₉ | C₄H₉ | H | H | ClO₄⁻ |
| | NK-1840 | (CH₂)₃SO₃⁻ | (CH₂)₃SO₃Na | H | H | ABSENT |
| | NK-9001 | (CH₂)₄SO₃⁻ | (CH₂)₄SO₃Na | H | H | ABSENT |
| | NK-9003 | C₄H₉ | C₄H₉ | H | H | ABSENT |
|  | NK-2929 | CH₃ | CH₃ | H | H | ClO₄⁻ |
| | NK-3375 | CH₃ | CH₃ | H | H | I⁻ |
| | NK-5056 | (CH₂)₄SO₃⁻ | (CH₂)₄SO₃·N(H)(C₂H₅) | SO₃Na | SO₃⁻ | ABSENT |
|  | NK-3266 | CH₃ | CH₃ | H | H | ClO₄⁻ |
| | NK-3620 | C₄H₉ | C₄H₉ | H | H | ClO₄⁻ |

F I G. 5
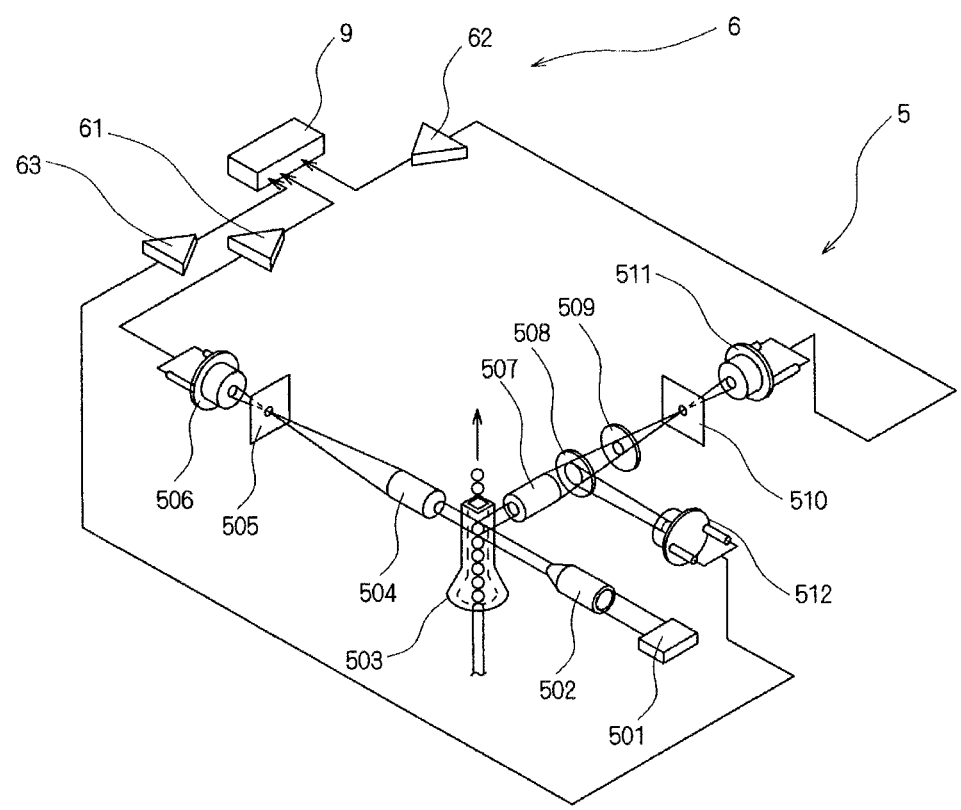

BLOOD ANALYZER, BLOOD ANALYZING METHOD, AND COMPUTER PROGRAM PRODUCT

RELATED APPLICATIONS

This application claims priority under 35 U.S.C. §119 to Japanese Patent Application No. 2009-076019 filed on Mar. 26, 2009 and 2009-294442 filed on Dec. 25, 2009, the entire contents of which are hereby incorporated by reference.

BACKGROUND OF THE INVENTION

1. Field of the Invention

The present invention relates to a blood analyzer, a blood analyzing method, and a computer program product, which are capable of measuring a blood sample to detect abnormal blood cells.

2. Description of the Related Art

Conventionally, there are known blood analyzers which are capable of: classifying formed elements of blood into, for example, red blood cells, white blood cells, and platelets; counting the classified elements; and allowing a measurement mode to be set for each measurement item. For example, U.S. Patent Application Publication No. 2008/0187990 discloses a sample analyzer that allows a user to set a measurement mode to a desired mode among the following two measurement modes: a CBC (Complete Blood Count) mode for measuring CBC measurement items that consist of a red blood cell count (RBC), white blood cell count (WBC), platelet count (PLT), hemoglobin content (HGB), hematocrit value (HCT), mean red blood cell volume (MCV), mean red blood cell hemoglobin (MCH), and a mean red blood cell hemoglobin concentration (MCHC); and a CBC+DIFF mode for measuring, in addition to the CBC measurement items, so-called DIFF measurement items with which to classify white blood cells into subclasses.

In the CBC mode, the aforementioned fundamental information about formed elements of blood can be obtained. In the CBC+DIFF mode, white blood cells are classified into subclasses and then counted, whereby more detailed information about the white blood cells can be obtained in addition to the fundamental information obtained by the CBC mode. Further, in the CBC+DIFF mode, abnormal blood cells such as immature white blood cells, which do not appear in the peripheral blood of a healthy person, can be detected as disclosed in U.S. Pat. No. 6,004,816.

As described above, information that can be obtained is different among each measurement mode. Therefore, in the case where it is necessary to detect presence of abnormal blood cells or abnormal distribution of white blood cells, the user is required to select a measurement mode different from the CBC mode, such as the CBC+DIFF mode.

In order to detect presence or absence of abnormal blood cells by using such a conventional sample analyzer as described in U.S. Patent Application Publication No. 2008/0187990, the user is required to perform the measurement in the CBC+DIFF mode.

SUMMARY OF THE INVENTION

The scope of the invention is defined solely by the appended claims, and is not affected to any degree by the statements within this summary.

A first aspect of the present invention is a blood analyzer comprising: a specimen preparation section for preparing, by using a blood sample obtained from a subject, a measurement specimen that is used to measure a white blood cell count among CBC measurement items; a measurement section for obtaining at least two types of optical information from blood cells contained in the measurement specimen prepared by the specimen preparation section by irradiating the measurement specimen with light; and a controller including a memory under control of a processor, the memory storing instructions enabling the processor to carry out operations comprising: classifying blood cells contained in the measurement specimen into at least white blood cells and blood cells suspected to be abnormal blood cells, based on the at least two types of optical information obtained by the measurement section; obtaining distribution data of the white blood cells and distribution data of the blood cells suspected to be abnormal blood cells; counting the white blood cells contained in the blood sample, based on the distribution data of the white blood cells; and determining presence or absence of the abnormal blood cells in the blood sample, based on the distribution data of the blood cells suspected to be abnormal blood cells.

A second aspect of the present invention is a blood analyzing method, using a blood analyzer which comprises: a specimen preparation section for preparing, by using a blood sample obtained from a subject, a measurement specimen that is used to measure a white blood cell count among CBC measurement items; and a measurement section for obtaining at least two types of optical information from blood cells contained in the measurement specimen prepared by the specimen preparation section by irradiating the measurement specimen with light, the blood analyzing method comprising: classifying blood cells contained in the measurement specimen into at least white blood cells and blood cells suspected to be abnormal blood cells contained in the measurement specimen, based on the at least two types of optical information obtained by the measurement section; obtaining distribution data of the white blood cells and distribution data of the blood cells suspected to be abnormal blood cells; counting the white blood cells contained in the measurement specimen, based on the distribution data of the white blood cells; and determining presence or absence of the abnormal blood cells in the blood sample, based on the distribution data of the blood cells suspected to be abnormal blood cells.

A third aspect of the present invention is a computer program product for a blood analyzer which comprises: a measurement apparatus for preparing, by using a blood sample obtained from a subject, a measurement specimen that is used to measure a white blood cell count among CBC measurement items, and for obtaining, by irradiating the measurement specimen with light, at least two types of optical information from blood cells contained in the measurement specimen; and a computer, the computer program product comprising a computer readable medium for storing instructions enabling the computer to carry out operations comprising: classifying blood cells contained in the measurement specimen into at least white blood cells and blood cells suspected to be abnormal blood cells contained in the measurement specimen, based on the at least two types of optical information obtained by the measurement section; obtaining distribution data of the white blood cells and distribution data of the blood cells suspected to be abnormal blood cells; counting the white blood cells contained in the blood sample, based on the distribution data of the white blood cells; and determining presence or absence of the abnormal blood cells in the blood sample, based on the distribution data of the blood cells suspected to be abnormal blood cells.

BRIEF DESCRIPTION OF THE DRAWINGS

FIG. 5 is a block diagram schematically illustrating structures of a detector and an analogue processing section according to the embodiment of the present invention;

DETAILED DESCRIPTION OF THE PREFERRED EMBODIMENTS

Hereinafter, an embodiment of a blood analyzer of the present invention will be described in detail with reference to the accompanying drawings.

Hereinafter, the present embodiment gives a specific description with reference to the drawings by taking, as an example, a blood analyzer that is capable of classifying formed elements of blood into, for example, red blood cells, white blood cells, and platelets, and counting the classified elements.

Note that, a term "white blood cell count" or "WBC" herein refers not to a white blood cell count that is obtained through counting white blood cells that have been classified into subclasses such as DIFF items, but to a total white blood cell count that is obtained through counting white blood cells that have not been classified into the subclasses.

Further, a term "abnormal blood cells" herein refers to blood cells that appear in larger numbers in the peripheral blood of ill patients than in the peripheral blood of healthy persons. A term "WBC-related abnormal blood cells" refers to abnormal cells which imply that the subject is ill of disease relating white blood cells. A term "PLT-related abnormal blood cells" refers to abnormal cells which imply that the subject is ill of disease relating platelets. A term "RBC-related abnormal blood cells" refers to abnormal cells which imply that the subject is ill of disease relating red blood cells.

Figure 1:
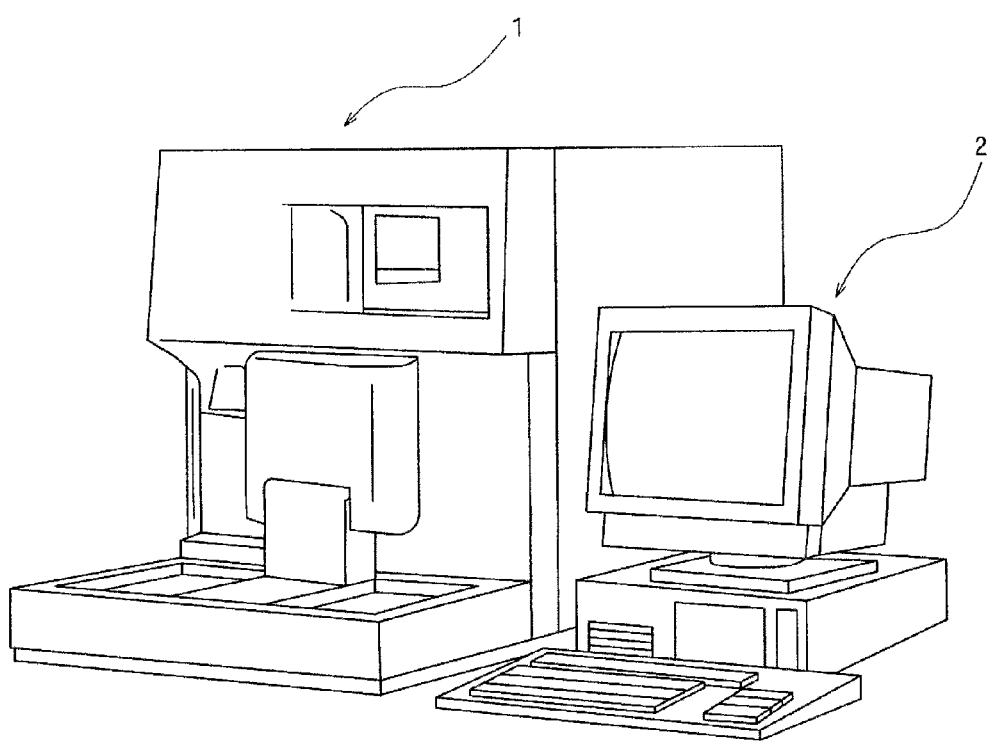
FIG. 1 is a perspective view schematically showing a structure of a blood analyzer according to an embodiment of the present invention.

FIG. 1 is a perspective view schematically showing a structure of the blood analyzer according to the embodiment of the present invention. As shown in FIG. 1, the blood analyzer according to the present embodiment includes a measurement apparatus (measurement unit) 1 and a calculation display apparatus 2 that is connected to the measurement apparatus 1 in a manner that allows the measurement apparatus 1 and the calculation display apparatus 2 to perform data communication therebetween.

The measurement apparatus 1 and the calculation display apparatus 2 are connected via a communication line that is not shown. The measurement apparatus 1 and the calculation display apparatus 2 perform data communication therebetween, through which the calculation display apparatus 2 controls the operation of the measurement apparatus 1. The calculation display apparatus 2 processes measurement data obtained by the measurement apparatus 1, thereby obtaining analysis results. The measurement apparatus 1 and the calculation display apparatus 2 may be connected via a network, or may be integrated to form a single apparatus. Within the single apparatus, data may be exchanged by interprocess communication or the like.

The measurement apparatus 1 uses the flow cytometry to detect characteristic information about, for example, white blood cells and reticulocytes contained in blood, and transmits results of the detection to the calculation display apparatus 2 as measurement data. The flow cytometry herein is a method in which a flow of a measurement specimen is formed; the specimen flow is irradiated with laser light; and forward scattered light, side scattered light, side fluorescence, and the like that occur due to particles (blood cells) contained in the measurement specimen as a result of the irradiation, are detected, whereby the particles (blood cells) contained in the measurement specimen are detected.

Figure 2:
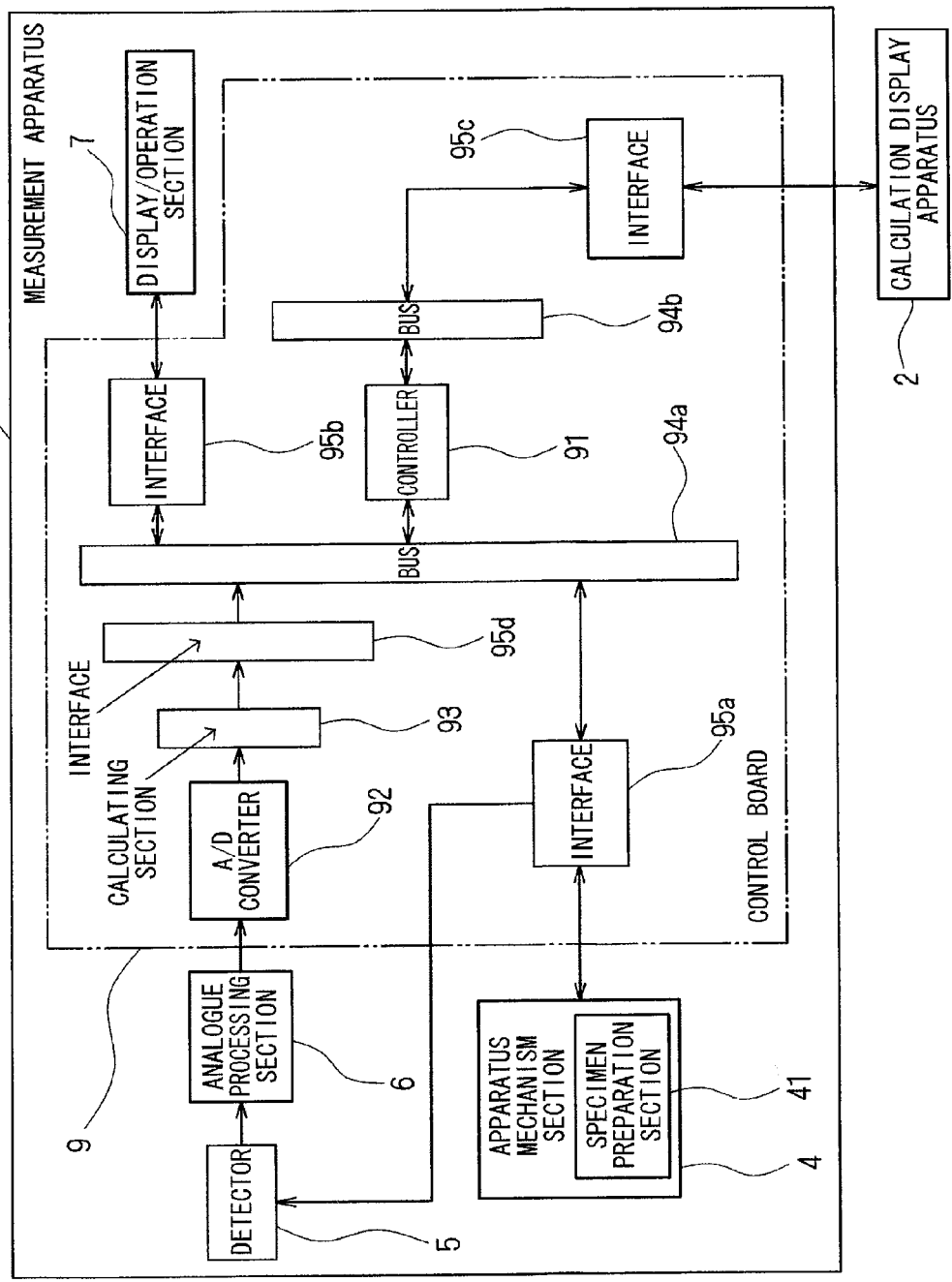
FIG. 2 is a block diagram showing a configuration of a measurement apparatus of the blood analyzer according to the embodiment of the present invention.

FIG. 2 is a block diagram showing a configuration of the measurement apparatus 1 of the blood analyzer according to the embodiment of the present invention. The measurement apparatus 1 includes an apparatus mechanism section 4, a detector 5 for performing measurement on a measurement specimen, an analogue processing section 6 for converting an output of the detector 5 into an analogue output, a display/operation section 7, and a control board 9 for controlling the operation of each above-described hardware component.

The control board 9 includes: controller 91 that has a control processor and a memory for causing the control processor to operate; and a 12-bit A/D converter 92 for converting signals, which are outputted from the analogue processing section 6, into digital signals; and a calculating section 93 for storing the digital signals outputted from the A/D converter 92 and for performing a process of selecting data to be outputted to the controller 91. The controller 91 is connected to the display/operation section 7 via a bus 94a and an interface 95b, and is connected to the calculation display apparatus 2 via a bus 94b and an interface 95c. The calculating section 93 outputs calculation results to the controller 91 via an interface 95d and the bus 94a. The controller 91 transmits the calculation results (i.e., measurement data) to the calculation display apparatus 2.

The apparatus mechanism section 4 is provided with a specimen preparation section 41 for preparing measurement specimens from reagents and blood. The specimen preparation section 41 prepares a WBC measurement specimen, an RET measurement specimen, a PLT measurement specimen, and the like by using an obtained sample and reagents.

Figure 3:
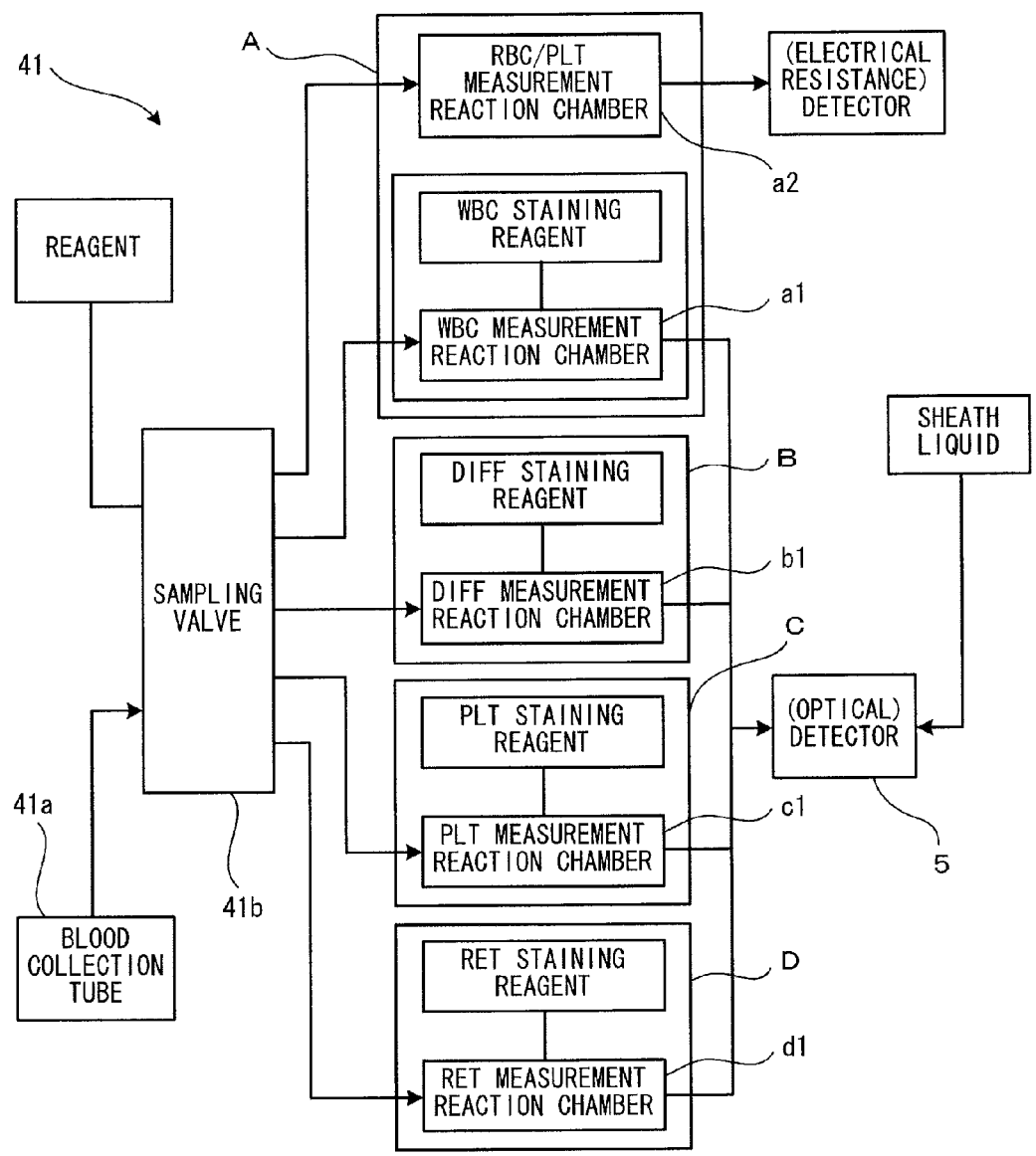
FIG. 3 is a block diagram schematically illustrating a configuration of a specimen preparation section according to the embodiment of the present invention.

FIG. 3 is a block diagram schematically illustrating a configuration of the specimen preparation section 41 according to the embodiment of the present invention. The specimen preparation section 41 includes a sampling valve 41b for aspirating blood and a plurality of reaction blocks A to D for preparing different measurement specimens for respective measurement modes that are selected.

The sampling valve 41b measures a fixed quantity of blood that has been aspirated from a blood collection tube 41a by an aspirating pipette (not shown).

The specimen preparation section 41 includes: a CBC measurement reaction block A for preparing specimens that are used for measuring CBC measurement items; a DIFF measurement reaction block B for preparing a specimen that is used for measuring DIFF items; a PLT measurement reaction block C for preparing a specimen that is used for measuring PLT items; and an RET measurement reaction block D for preparing a specimen that is used for measuring RET items.

The CBC measurement reaction block A prepares measurement specimens for measuring WBC, RBC, and PLT. To be specific, the CBC measurement reaction block A includes a mechanism for preparing a measurement specimen that is used for measuring a white blood cell count (WBC). The mechanism includes a WBC staining reagent and a WBC measurement reaction chamber a1. The CBC measurement reaction block A further includes a mechanism for preparing a measurement specimen that is used for measuring a red blood cell count (RBC) and a platelet count (PLT). The mechanism includes an RBC/PLT measurement reaction chamber a2.

The DIFF measurement reaction block B includes a mechanism for preparing a measurement specimen that is used for measuring DIFF items. The mechanism includes a DIFF staining reagent and a DIFF measurement reaction chamber b1.

The PLT measurement reaction block C includes a mechanism for preparing a measurement specimen that is used for measuring PLT items. The mechanism includes a PLT staining reagent and a PLT measurement reaction chamber c1.

The RET measurement reaction block D includes a mechanism for preparing a measurement specimen that is used for measuring RET items. The mechanism includes an RET staining reagent and an RET measurement reaction chamber d1.

The RBC/PLT measurement reaction chamber a2 is connected to the sampling valve 41b, and is configured to mix the fixed quantity of blood, which is measured by the sampling valve 41b, with a reagent. The RBC/PLT measurement reaction chamber a2 is connected to an electrical resistance detector, and is configured to supply the measurement specimen prepared at the RBC/PLT measurement reaction chamber a2 to the electrical resistance detector. Thus, the specimen preparation section 41 is capable of preparing measurement specimens in which the whole blood is diluted. Note that the present embodiment provides detailed descriptions of features relating to measurement of WBC among the CBC measurement items, and detailed descriptions of features relating to measurement of RBC and PLT are omitted.

The reaction chambers a1 to d1 are each connected to the sampling valve 41b, and configured to be able to mix a predetermined amount of stain solution into a mixture of a reagent and the fixed quantity of blood measured by the sampling valve 41b. Also, the reaction chambers a1 to d1 are each connected to the detector 5 that is an optical detector. Each of the reaction chambers a1 to d1 is configured to supply the detector 5 with a measurement specimen that is prepared by mixing the blood with a predetermined reagent and a predetermined stain solution.

Accordingly, by performing specimen preparation at the WBC measurement reaction chamber a1 of the CBC measurement reaction block A, the specimen preparation section 41 can prepare, as a WBC measurement specimen, a measurement specimen in which white blood cells are stained and red blood cells are hemolyzed. Further, by performing specimen preparation at the DIFF measurement reaction chamber b1 of the DIFF measurement reaction block B, the specimen preparation section 41 can prepare, as a DIFF measurement specimen, a measurement specimen in which white blood cells in different subclasses are stained such that a difference in fluorescence occurs in accordance with each subclass, and in which red blood cells are hemolyzed. Still further, by performing specimen preparation at the RET measurement reaction chamber d1 of the RET measurement reaction block D, the specimen preparation section 41 can prepare, as an RET measurement specimen, a measurement specimen in which reticulocytes are stained. Still further, by performing specimen preparation at the PLT measurement reaction chamber c1 of the PLT measurement reaction block C, the specimen preparation section 41 can prepare, as a PLT measurement specimen, a measurement specimen in which platelets are stained. These prepared measurement specimens are each supplied, together with a sheath liquid, to a below-described sheath flow cell provided in the (optical) detector 5.

As described later, the blood analyzer 1 according to the embodiment of the present invention is configured to be able to set a plurality of measurement modes. The blood analyzer 1 is configured to prepare measurement specimens corresponding to the set measurement modes, and perform measurement on measurement items corresponding to the set measurement modes. The plurality of measurement modes include: measurement modes each for measuring a single measurement item; and measurement modes each for measuring a combination of multiple measurement items. Measurement items of the present embodiment include CBC, DIFF, RET, and PLT. The blood analyzer 1 is capable of setting, as the measurement modes each for measuring a single measurement item, the following four kinds of measurement modes: (1) a CBC mode; (2) a DIFF mode; (3) an RET mode; and (4) a PLT mode.

The blood analyzer 1 is further capable of setting, as the measurement modes each for measuring a combination of multiple measurement items, six kinds of measurement modes as shown below:
 (5) CBC+DIFF mode
 (6) CBC+RET mode
 (7) CBC+PLT mode
 (8) CBC+DIFF+RET mode
 (9) CBC+DIFF+PLT mode
 (10) CBC+DIFF+RET+PLT mode The blood analyzer 1 according to the present embodiment is capable of selecting one of the above ten kinds of measurement modes to perform measurement. To be specific, when a measurement mode is selected at the calculation display apparatus 2, the calculation display apparatus 2 transmits, to the controller 91 of the measurement apparatus 1, an instruction signal that provides an instruction to prepare a measurement specimen used for measuring items that are to be measured in the selected measurement mode, and to measure the prepared measurement specimen. Upon receiving the instruction signal, the controller 91 controls the specimen preparation section 41 so as to prepare the measurement specimen by using, among the reaction blocks A to D, a reaction block that is provided for preparing the measurement specimen.

For example, when the CBC measurement mode is selected, the controller 91 controls the specimen preparation section 41 so as to prepare, using the CBC measurement reaction block A, measurement specimens for measuring the CBC measurement items. To be more specific, the controller 91 controls the specimen preparation section 41 so as to prepare, using the WBC measurement reaction chamber a1, a measurement specimen for measuring WBC among the CBC measurement items, and so as to prepare, using the RBC/PLT measurement reaction chamber a2, a measurement specimen for measuring RBC and PLT among the CBC measurement items.

Whereas, when the DIFF measurement mode is selected, the controller 91 controls the specimen preparation section 41 so as to prepare, using the DIFF measurement reaction block B, a measurement specimen for measuring the DIFF measurement items.

Further, when the CBC+DIFF measurement mode is selected, the controller 91 controls the specimen preparation section 41 so as to prepare, using the CBC measurement reaction block A, the measurement specimens for measuring the CBC measurement items, and so as to prepare, using the DIFF measurement reaction block B, the measurement specimen for measuring the DIFF measurement items.

Note that the WBC staining reagent of the CBC measurement reaction block A contains a fluorescent dye that stains white blood cells so that the white blood cells can be distinguished from the other particles contained in the blood. The fluorescent dye is at least one selected from the group consisting of: a fluorescent dye represented by the following general formula (I):

[chemical formula I]

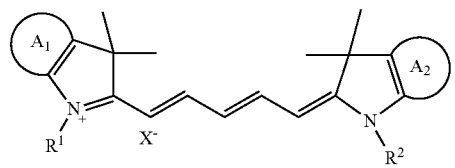

(I)

(In the formula, $R^1$ and $R^2$ are identical to or different from each other, and are each an alkyl group;

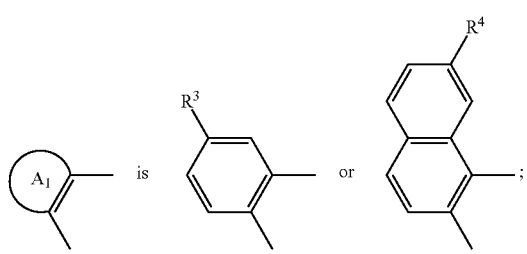

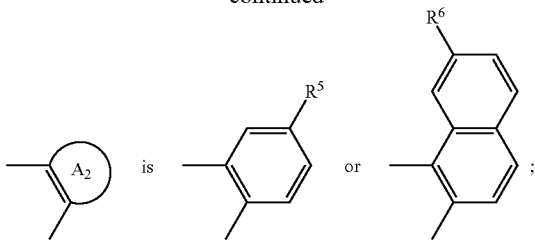

$R^3$, $R^4$, $R^5$ and $R^6$ are identical to or different from each other, and are each a hydrogen atom or an alkyl group; and $X^-$ is an anion); and a fluorescent dye represented by the following general formula (II):

[chemical formula II]

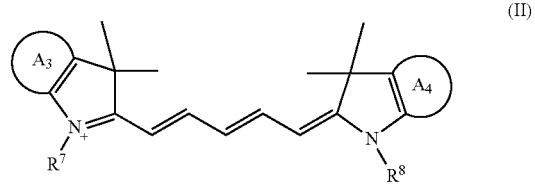

(II)

(In the formula, $R^7$ and $R^8$ are identical to or different from each other, and are each an alkyl group that may have an acid group;

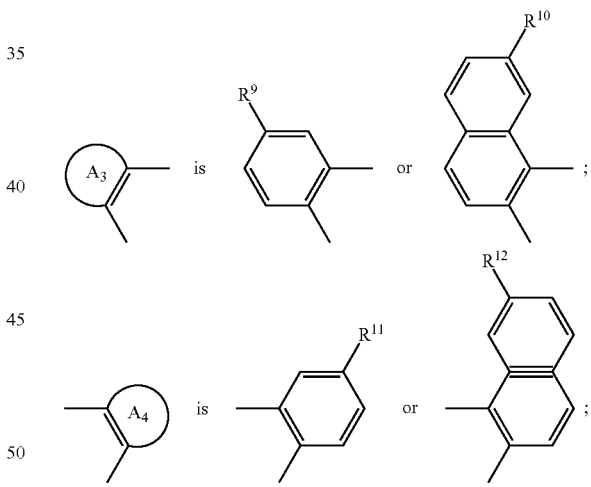

$R^9$, $R^{10}$, $R^{11}$, and $R^{12}$ are identical to or different from each other, and are each a hydrogen atom or an acid group, and an acid group exists in at least one of $R^7$ to $R^{12}$; and the acid group that may exist in $R^7$ to $R^{12}$ may form a salt. However, at least one of the acid groups that may exist in $R^7$ to $R^{12}$ is a group from which a proton has been released).

Figure 4:
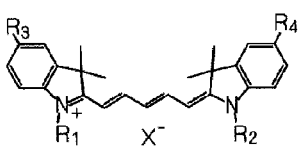
FIG. 4 shows chemical structures of fluorescent dyes to be contained in a WBC staining reagent.
Figure 4:
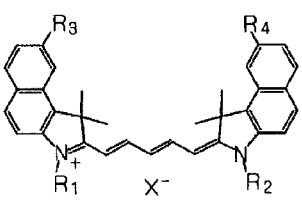
Figure 4:
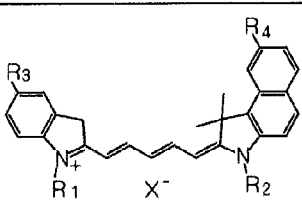

FIG. 4 shows chemical structures of specific fluorescent dyes represented by the general formulas (I) and (II), and the names of the dyes having these chemical structures.

FIG. 4 shows chemical formulas of the fluorescent dyes to be contained in the WBC staining reagent. Specifically, as shown in FIG. 4, fluorescent dyes, such as NK-529, NK-2670, NK-3750, NK-3383, NK-1840, NK-9001 NK-9003, NK-2929, NK-3375, NK-5056, NK-3266, and NK-3620, are used, for example. Any of the above fluorescent dyes can be purchased from Hayashibara Biochemical Laboratories, Inc.

The DIFF staining reagent contains a fluorescent dye for staining white blood cells in different subclasses, such that a difference in fluorescence occurs in accordance with each subclass. Used as the DIFF staining reagent, which contains such a fluorescent dye, may be a reagent disclosed in U.S. Pat. No. 6,004,816, for example. U.S. Pat. No. 6,004,816 is hereby incorporated by reference in its entirety as though fully and completely set forth herein.

The PLT staining reagent contains a fluorescent dye for staining platelets contained in blood so that the platelets can be distinguished from the other particles in the blood. Used as the PLT staining reagent, which contains such a fluorescent dye, may be a reagent disclosed in U.S. Patent Application Publication No. 2008/0102526, for example.

The RET staining reagent contains a fluorescent dye for staining reticulocytes contained in blood so that the reticulocytes can be distinguished from the other particles in the blood. Used as the RET staining reagent, which contains such a fluorescent dye, may be a reagent disclosed in U.S. Patent Application Publication No. 2008/0102526, for example. U.S. Patent Application Publication No. 2008/0102526 is hereby incorporated by reference in its entirety as though fully and completely set forth herein.

FIG. 5 is a block diagram schematically illustrating structures of the detector 5 and the analogue processing section 6 according to the embodiment of the present invention. As shown in FIG. 5, the detector 5 includes a light emitter 501 for emitting laser light; an irradiation lens unit 502; a sheath flow cell 503 to be irradiated with the laser light; a condenser lens 504 disposed on an extension of the advancing direction of the laser light emitted from the light emitter 501; a pinhole 505; a PD (photodiode) 506 (a beam stopper that is not shown is disposed between the sheath flow cell 503 and the condenser lens 504), a condenser lens 507 disposed in a direction that intersects the advancing direction of the laser light emitted from the light emitter 501; a dichroic mirror 508; an optical filter 509; a pinhole 510; an APD (avalanche photodiode) 511; and a PD (photodiode) 512 disposed laterally to the dichroic mirror 508.

The light emitter 501 is provided for emitting light toward a flow of a measurement specimen passing through the inside of the sheath flow cell 503. The irradiation lens unit 502 is provided for irradiating the specimen flow with the light emitted from the light emitter 501. The PD 506 is provided for receiving forward scattered light emitted from the sheath flow cell 503. Note that, based on the forward scattered light emitted from the sheath flow cell 503, information about the sizes of particles (blood cells) contained in the measurement specimen can be obtained.

The dichroic mirror 508 is provided for separating side scattered light and side fluorescence that are emitted from the sheath flow cell 503. To be specific, the dichroic mirror 508 is provided for causing the side scattered light emitted from the sheath flow cell 503 to enter the PD 512, and for causing the side fluorescence emitted from the sheath flow cell 503 to enter the APD 511. The PD 512 is provided for receiving the side scattered light. Based on the side scattered light emitted from the sheath flow cell 503, information about the inside of the particles (blood cells) contained in the measurement specimen (e.g., the size of the nucleus of each particle) can be obtained.

The APD 511 is provided for receiving the side fluorescence. When fluorescent substances such as stained blood cells are irradiated with light, light having a wavelength longer than that of the irradiated light occurs. The intensity of the side fluorescence increases in accordance with an increase in the degree of staining of the blood cells. Accordingly, by measuring the intensity of the side fluorescence emitted from the sheath flow cell 503, characteristic information about the degree of staining of the blood cells can be obtained. Therefore, in the CBC mode using a fluorescent dye that can specifically stain white blood cells, the white blood cells can be distinguished from the other blood cells in the blood and counted, based on a difference in the side fluorescence intensity. The PD 506, 512, and APD 511 convert received light signals into electrical signals. The electrical signals resulting from the conversions by the PD 506, 512, and APD 511 are amplified by amplifiers 61, 63, and 62, respectively, and are outputted to the control board 9.

Figure 6:
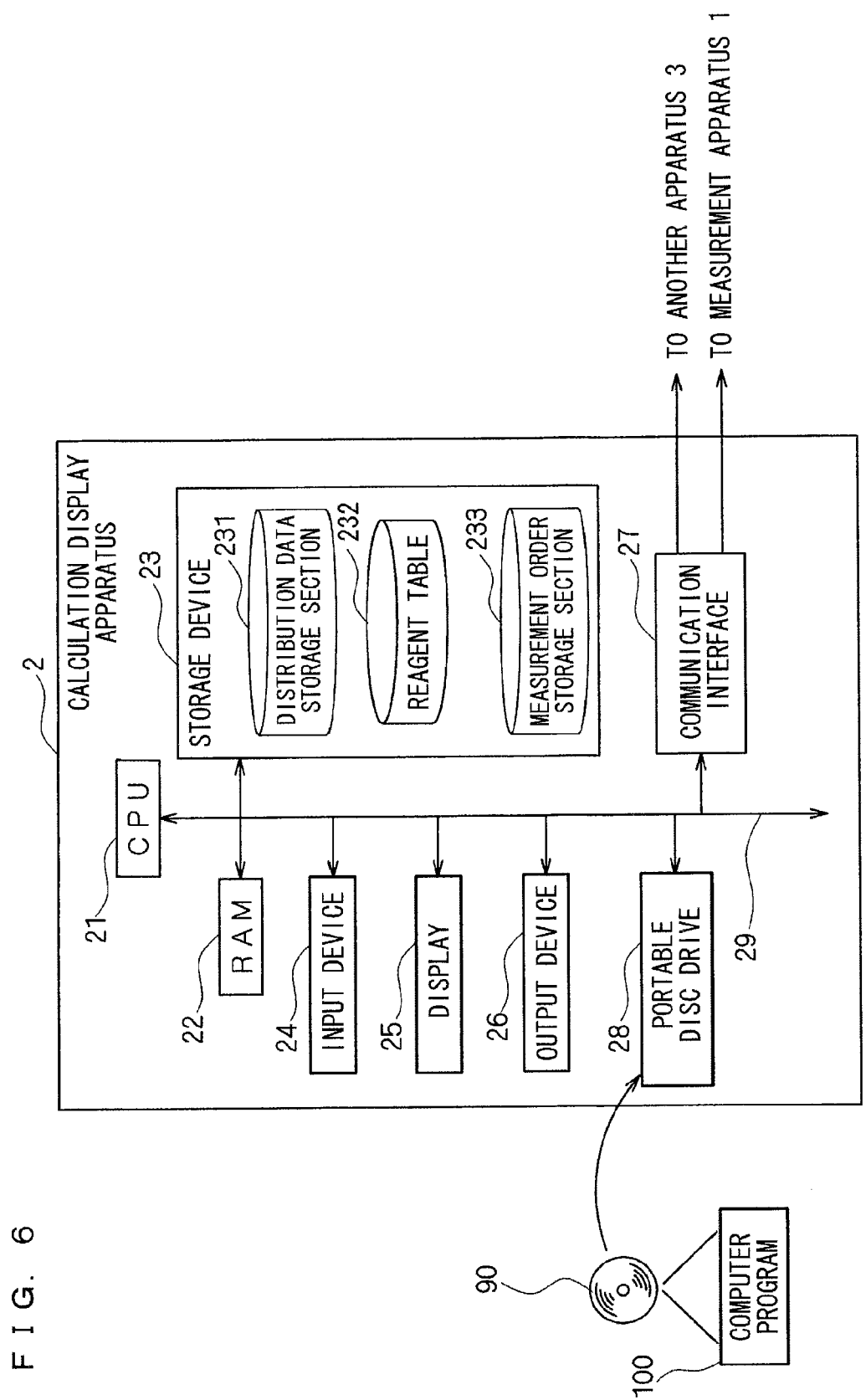
FIG. 6 is a block diagram showing a configuration of a calculation display apparatus of the blood analyzer according to the embodiment of the present invention.

FIG. 6 is a block diagram showing a configuration of the calculation display apparatus 2 of the blood analyzer according to the embodiment of the present invention. As shown in FIG. 6, the calculation display apparatus 2 includes a CPU (Central Processing Unit) 21, a RAM 22, a storage device 23, an input device 24, a display 25, an output device 26, a communication interface 27, a portable disc drive 28, and an internal bus 29 for connecting these hardware components. The CPU 21 is connected to the above hardware components of the calculation display apparatus 2 via the internal bus 29. The CPU 21 executes various software functions in accordance with a computer program 100 stored in the storage device 23. The RAM 22 is configured as a volatile memory such as an SRAM, SDRAM, or the like. At the execution of the computer program 100, a load module is loaded into the RAM 22. The RAM 22 stores, for example, temporary data generated at the execution of the computer program 100.

The storage device 23 is structured, for example, as an embedded fixed storage device (hard disk), a volatile memory such as an SRAM, or a non-volatile memory such as a ROM. The computer program 100 to be stored in the storage device 23 is downloaded by the portable disc drive 28 from a portable storage medium 90 that is, for example, a DVD or CD-ROM having stored therein information such as a program, data, and the like. At the execution of the computer program 100, the computer program 100 is loaded from the storage device 23 into the RAM 22 and then executed. Of course, the computer program 100 may be downloaded via the communication interface 27 from an external computer that is connected to a network to which the calculation display apparatus 2 is connected.

The storage device 23 includes a distribution data storage section 231 for storing distribution data that is generated based on the measurement data obtained by the measurement apparatus 1; a reagent table 232 for storing types and amounts of reagents that are each used in a corresponding measurement mode; and a measurement order storage section 233 for storing measurement orders.

The measurement order storage section 233 stores each measurement order in association with a corresponding sample number. Each measurement order includes information about measurement items to be measured for the corresponding sample; and subject information such as the age, case history, and the like of a subject from whom the corresponding sample has been collected. The measurement orders are inputted by a user via the input device 24 of the calculation display apparatus 2, to be stored in the measurement order storage section 233.

The CPU 21 performs processing illustrated in a below-described flowchart to analyze the distribution data stored in the distribution data storage section 231, thereby creating a two-dimensional scattergram, and detects abnormal blood cells based on the distribution data. Note that the distribution data storage section 231, the reagent table 232, and the measurement order section 233 may not necessarily be included in the storage device 23, but may be included in an external computer and may be referred to via the communication interface 27.

The communication interface 27 is connected to the internal bus 29. By being connected to the measurement apparatus 1 via the communication line, the communication interface 27 can perform data transmission/reception with the measurement apparatus 1. To be specific, the communication interface 27 transmits, to the measurement apparatus 1, instruction information or the like that provides an instruction to start measurement, and receives measurement data and the like. The communication interface 27 is further capable of performing data transmission/reception with another device 3 that is connected to the communication interface 27 via a network. This makes it possible to collect measurement data obtained by a plurality of measurement apparatuses 1, and analyze the measurement data.

The input device 24 is a data input medium that includes a keyboard, a mouse, and the like. The display 25 is, for example, a CRT monitor or an LCD for displaying analysis results in a graphical manner. The output device 26 is, for example, a printer such as a laser printer, an ink-jet printer, or the like.

Figure 7:
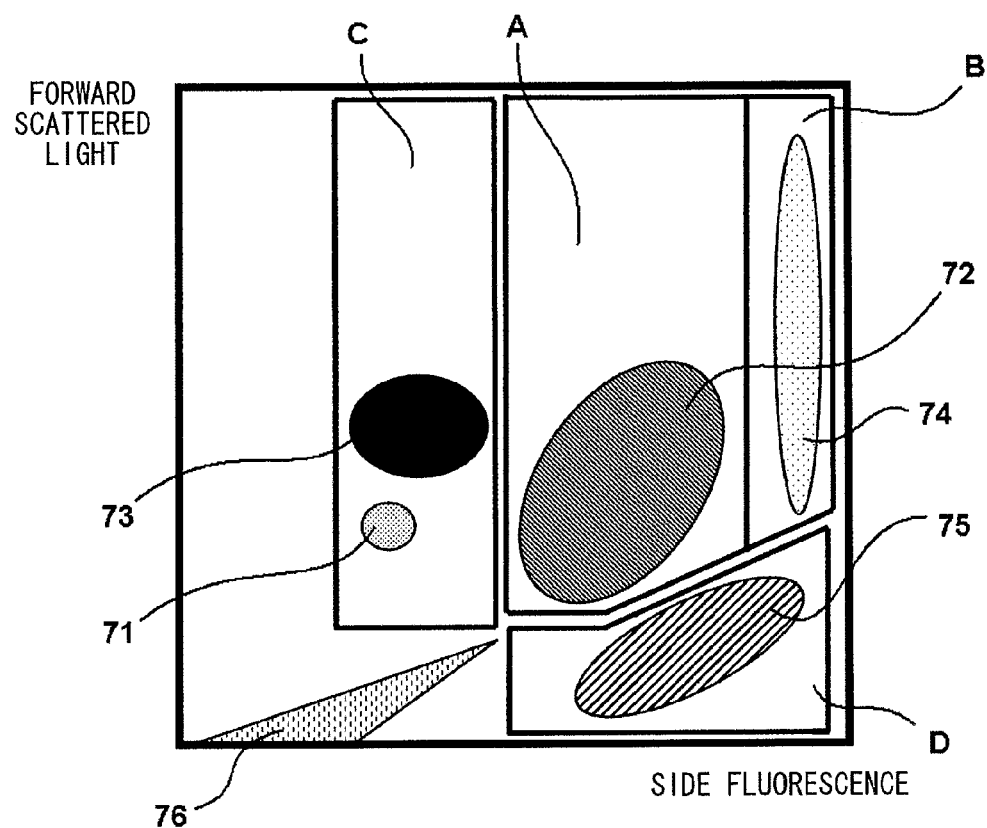
FIG. 7 illustrates a scattergram that is created in the case where a white blood cell count is measured in a CBC mode.

FIG. 7 illustrates a scattergram that is created in the case where white blood cells are counted in the CBC mode using the aforementioned reagent. In FIG. 7, the vertical axis represents the forward scattered light intensity and the horizontal axis represents the side fluorescence intensity.

As shown in FIG. 7, appearing on the scattergram that is created in the case where white blood cells are counted in the CBC mode, are mainly Howell-Jolly bodies 71, white blood cells 72, nucleated red blood cells 73, WBC-related abnormal blood cells 74, PLT-related abnormal blood cells 75, and debris 76 containing hemolyzed red blood cells. The nucleated red blood cells 73, the WBC-related abnormal blood cells 74, and the PLT-related abnormal blood cells 75 do not appear when the peripheral blood of a healthy person is measured. Note that the WBC-related abnormal blood cells 74 include immature white blood cells and the like, and the PLT-related abnormal blood cells 75 include reticulated platelets, giant platelets, platelet aggregation, and the like.

In the present embodiment, a plurality of regions are set on the scattergram as shown in FIG. 7, and particles appearing in each region are counted. To be specific, a region A in which the white blood cells 72 appear, a region B for detecting the WBC-related abnormal blood cells 74, a region C in which the nucleated red blood cells 73 appear, and a region D for detecting the PLT-related abnormal blood cells 75, are set on the scattergram. Accordingly, in the case where white blood cells are counted in the CBC mode, the particles appearing in the region A are counted. The result of the counting is used as a white blood cell count.

When a large number of particles are distributed in a region in which particles are not normally distributed, it is conceivable that abnormal blood cells are present. Accordingly, in the present embodiment, the regions B, C, and D are set, on the scattergram, in regions where particles are not normally distributed. Then, it is determined for each of the regions B, C, and D whether or not a predetermined number or more of particles are present therein.

When it has been determined that a predetermined number or more of particles are present in any of the regions B, C, and D, it can be determined that presence of abnormal blood cells has been detected. In this case, for the purpose of performing analysis on more detailed measurement items, a selection of, for example, the CBC+DIFF mode is received, and thereby reagents used for measurement specimen preparation are changed. Accordingly, more detailed analysis data can be obtained. Further, when the abnormal blood cells have been detected, a type of blood component relating to the appearing abnormal blood cells can be known since the regions B, C, and D are separately set. That is, the region in which the abnormal blood cells have been detected can serve as a clue for a user to determine which detailed measurement items are to be analyzed.

Although it was difficult to detect abnormal blood cells contained in a blood sample by using conventional sample analyzers with optical detection in the CBC mode, the inventors of the present invention discovered that it was possible to detect abnormal blood cells by optically detecting blood cells contained in the blood sample in the CBC mode using a staining reagent that contains the aforementioned fluorescent dye. For this reason, unless it is determined that analysis on detailed measurement items is necessary, the user does not need to select a measurement mode different from the CBC mode, such as the CBC+DIFF mode, the CBC+RET mode, or the like. This reduces the necessity to use such a reagent as disclosed in U.S. Pat. No. 6,004,816, which is dedicated to classifying white blood cells into five categories. Accordingly, the cost of reagents to be used is reduced, and as a result, the cost of the entire measurement can be suppressed.

Figure 8:
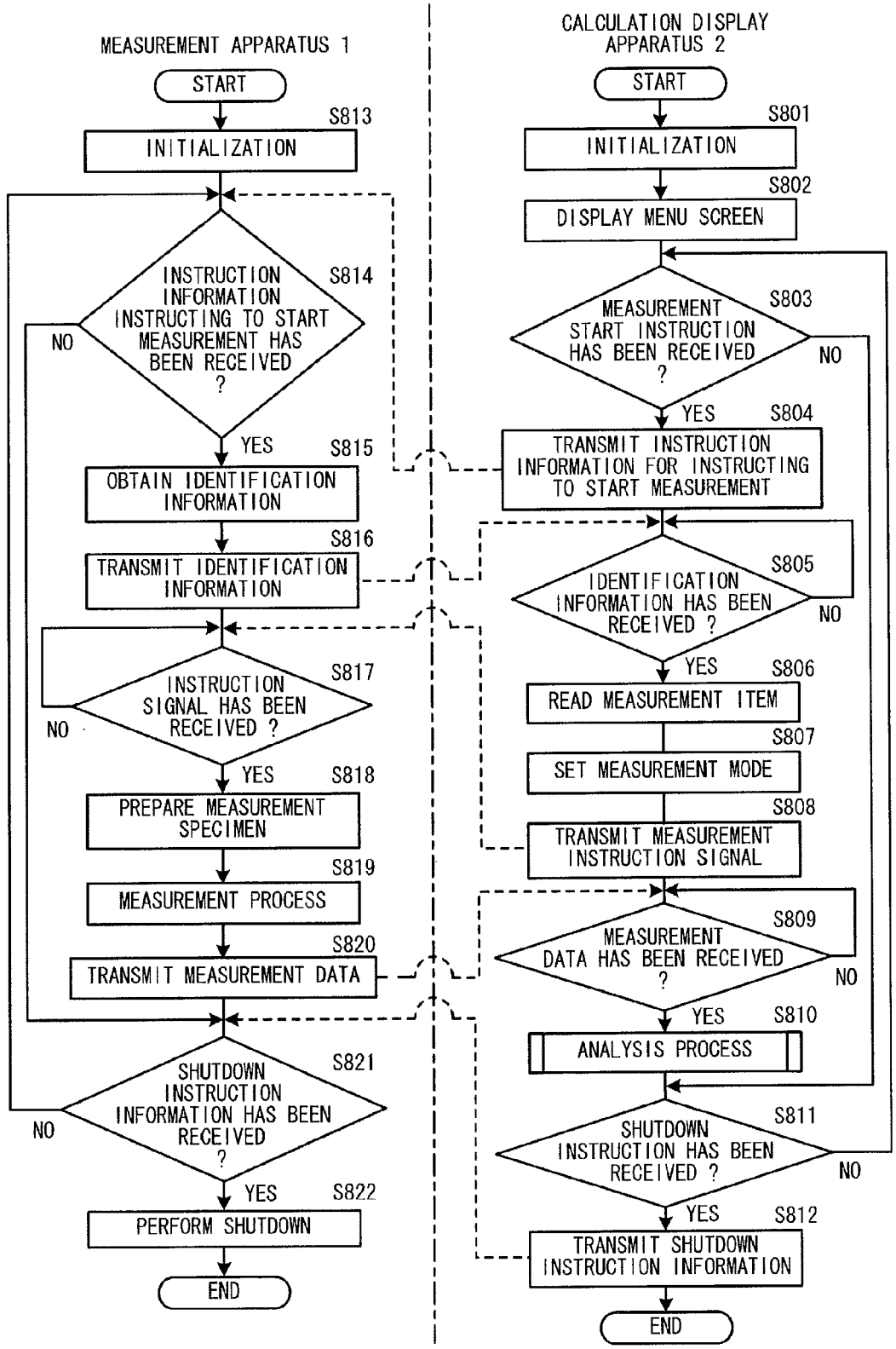
FIG. 8 is a flowchart showing steps of processing performed by a controller of a control board of the measurement apparatus and steps of processing performed by a CPU of the calculation display apparatus, according to the embodiment of the present invention.

FIG. 8 is a flowchart showing steps of processing performed by the controller 91 of the control board 9 of the measurement apparatus 1 and steps of processing performed by the CPU 21 of the calculation display apparatus 2, according to the embodiment of the present invention.

In FIG. 8, when detecting that the measurement apparatus 1 has started, the controller 91 of the control board 9 of the measurement apparatus 1 performs initialization (step S813), in which the controller 91 performs an operation check for each component of the measurement apparatus 1. Also, when detecting that the calculation display apparatus 2 has started, the CPU 21 of the calculation display apparatus 2 performs initialization (of a program) (step S801), and displays a menu screen on the display 25 (step S802). Through the menu screen, inputting of a measurement order, receiving of a selection of a measurement mode such as the CBC mode, the CBC+DIFF mode, the RET mode, or the like, and receiving of a measurement start instruction and a shutdown instruction, can be performed, for example.

The CPU 21 of the calculation display apparatus 2 determines whether or not a measurement start instruction has been received (step S803). When the CPU 21 has determined that the measurement start instruction has not been received (step S803: NO), the CPU 21 skips steps S804 to S810. When the CPU 21 has determined that the measurement start instruction has been received (step S803: YES), the CPU 21 transmits, to the measurement apparatus 1, instruction information that provides an instruction to start measurement (step S804). The controller 91 of the control board 9 of the measurement apparatus 1 determines whether or not the instruction information that provides the instruction to start measurement has been received (step S814). When the controller 91 has determined that the instruction information that provides the instruction to start measurement has been received (step S814: YES), the controller 91 causes a bar code reader (not shown) to read a bar code label (not shown) affixed to a container that contains blood, thereby obtaining identification information of the blood (sample ID) (step S815). When the controller 91 has determined that the instruction information that provides the instruction to start measurement has not been received (step S814: NO), the controller 91 skips steps S815 to S820.

The controller 91 transmits the obtained identification information (sample ID) to the calculation display apparatus 2 (step S816). The CPU 21 of the calculation display apparatus 2 determines whether or not the identification information (sample ID) has been received (step S805). When the CPU 21 has determined that the identification information (sample ID) has not been received (step S805: NO), the CPU 21 enters a standby state. When the CPU 21 has determined that the identification information (sample ID) has been received (step S805: YES), the CPU 21 refers to the measurement order storage section 233 of the storage device 23 based on the identification information (sample ID), thereby reading measurement items included in a measurement order that is stored in association with the identification information (sample ID) (step S806). Based on the read measurement items, the CPU 21 sets a measurement mode (step S807). Then, the CPU 21 transmits, to the measurement apparatus 1, a signal that provides an instruction to prepare and measure a measurement specimen in accordance with the set measurement mode (step S808).

Hereinafter, the above processing will be described in detail. The storage device 23 of the calculation display apparatus 2 stores the reagent table 232 that stores the names of the reagents to be used for preparing the measurement specimens corresponding to the respective measurement modes. When the measurement mode is set at step S807, the CPU 21 refers to the reagent table 232 by using the set measurement mode as key information, thereby determining a reagent (i.e., a reaction block) that is to be used for preparing a measurement specimen. The CPU 21 transmits, to the controller 91 of the measurement apparatus 1, a signal that provides an instruction to prepare the measurement specimen by using the determined reaction block and to measure the prepared measurement specimen by using the detector 5. Note that the set measurement mode is stored in the storage device 23 of the calculation display apparatus 2.

Next, the controller 91 of the control board 9 of the measurement apparatus 1 determines whether or not the instruction signal has been received (step S817). When the controller 91 has determined that the instruction signal has not been received (step S817: NO), the controller 91 enters a standby state. When the controller 91 has determined that the instruction signal has been received (step S817: YES), the controller 91 controls the specimen preparation section 41 so as to prepare the measurement specimen corresponding to the received measurement mode (step S818), and starts a process of measuring the measurement specimen (step S819).

To be specific, when the controller 91 has received an instruction signal that provides an instruction to prepare and measure measurement specimens in the CBC measurement reaction block A, the controller 91 controls the operation of the specimen preparation section 41 so as to introduce, into the WBC measurement reaction chamber a1 of the CBC measurement reaction block A, blood of the fixed quantity measured at the sampling valve 41b and a reagent (a hemolytic agent), and so as to introduce the WBC staining reagent into the WBC measurement reaction chamber a1. In this manner, the WBC measurement specimen is prepared. The controller 91 performs a process of introducing the prepared WBC measurement specimen into the detector 5. Then, electrical signals corresponding to the intensity of received side scattered light, the intensity of received side fluorescence, and the intensity of received forward scattered light are outputted to the control board 9 via the detector 5 and the analogue processing section 6. The A/D converter 92 of the control board 9 converts these obtained analogue signals into, for example, 12-bit digital signals. The calculating section 93 performs predetermined processing on the digital signals outputted from the A/D converter 92, and provides resultant integer sequence information to the controller 91. The controller 91 transmits the received integer sequence information to the calculation display apparatus 2, as measurement data (step S820).

The CPU 21 determines whether or not the measurement data has been received (step S809). When the CPU 21 has determined that the measurement data has been received (step S809: YES), the CPU 21 performs an analysis process based on the received measurement data (step S810). When the CPU 21 has determined that the measurement data has not been received (step S809: NO), the CPU 21 enters a standby state.

Figure 9:
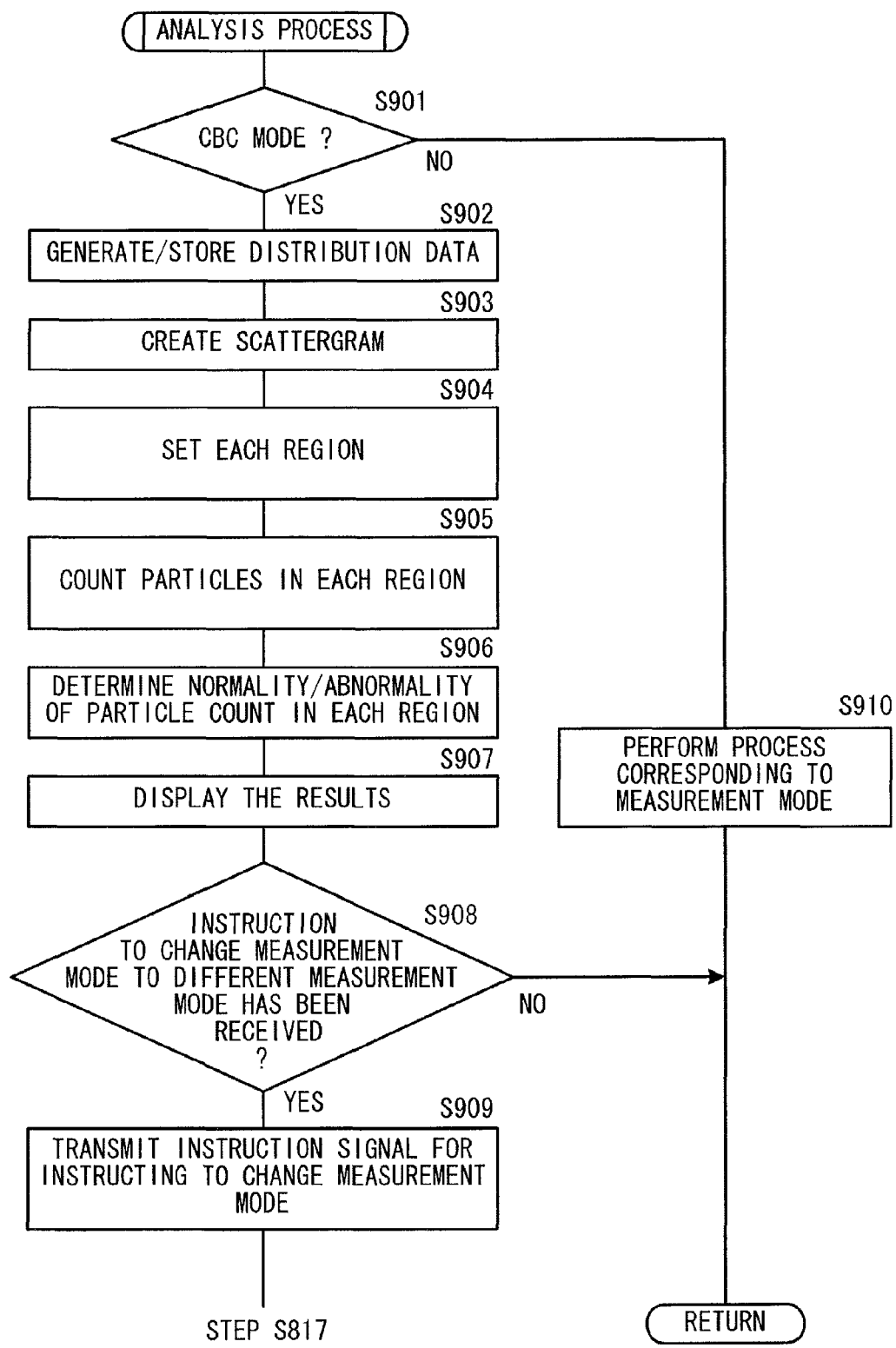
FIG. 9 is a flowchart showing steps of an analysis process that is performed by the CPU of the calculation display apparatus according to the embodiment of the present invention.

FIG. 9 is a flowchart showing steps of the analysis process that is performed at step S810 in FIG. 8 by the CPU 21 of the calculation display apparatus 2 according to the embodiment of the present invention. In FIG. 9, based on the received measurement data, the CPU 21 of the calculation display apparatus 2 reads, from the storage device 23, the measurement mode, in which the sample measurement has been performed and thereby the measurement data has been obtained, and the CPU 21 determines whether or not the measurement mode is the CBC mode (step S901).

When the CPU 21 has determined that the measurement mode is the CBC mode (step S901: YES), the CPU 21 generates, for each particle contained in the sample, distribution data that contains two parameters which have been obtained for said each particle, the two parameters representing the forward scattered light intensity and the side fluorescence intensity. The CPU 21 associates the generated distribution data with subject information, and stores the distribution data in the distribution data storage section 231 of the storage device 23 (step S902). The CPU 21 creates a scattergram as shown in FIG. 7, on which the distribution data is plotted based on the forward scattered light intensity and the side fluorescence intensity (step S903).

The CPU 21 sets, on the scattergram, a WBC region for counting white blood cells, an abnormal-WBC region for detecting WBC-related abnormal blood cells, an abnormal-RBC region for detecting nucleated red blood cells, and an abnormal-PLT region for detecting PLT-related abnormal blood cells (step S904). FIGS. 10A to 10D each illustrate a scattergram on which the WBC region, the abnormal-WBC region, the abnormal-PLT region, and the abnormal-RBC region are set (i.e., gating).

FIG. 10A to FIG. 10D illustrate scattergrams that were obtained as a result of measuring blood collected from a plurality of patients. In each scattergram, the vertical axis represents the forward scattered light intensity and the horizontal axis represents the side fluorescence intensity. Each scattergram shows a WBC region 101, an abnormal-WBC region 102, an abnormal-PLT region 103, and an abnormal-RBC region 104.

Figure 10A:
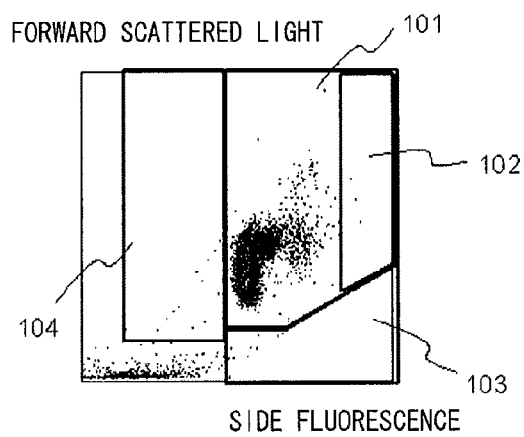
FIG. 10A to FIG. 10D illustrate scattergrams, in each of which a WBC region, an abnormal-WBC region, an abnormal-PLT region, and an abnormal-RBC region are set (i.e., gating)

FIG. 10A is a scattergram that was obtained as a result of measuring blood collected from a healthy person.

Figure 10B:
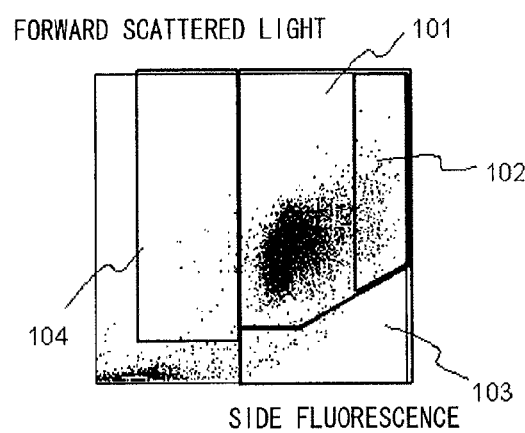

FIG. 10B is a scattergram that was obtained as a result of measuring blood collected from a patient with leukemia. An experiment was conducted, in which red blood cells of the blood of the patient were hemolyzed to prepare a smear, and immature granulocytes contained in the prepared smear were visually counted. As a result, it was observed that the immature granulocytes, which are not found in the blood of a healthy person, account for 8% of a total white blood cell count.

Figure 10C:
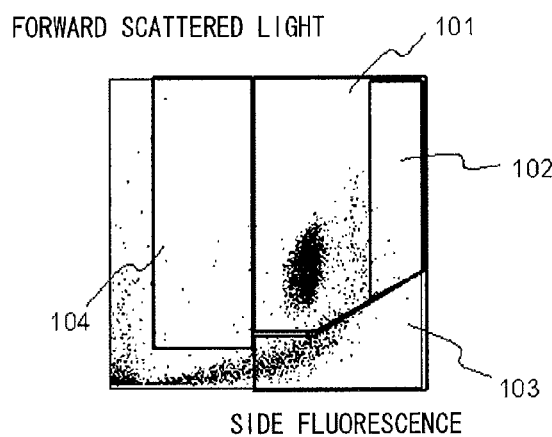

FIG. 10C is a scattergram that was obtained as a result of measuring blood collected from a patient with thrombocytopenia. An experiment was conducted, in which reticulated platelets contained in the blood of the patient were counted by a blood cell counter XE-2100 (manufactured by Sysmex Corporation). As a result, the obtained reticulated platelet count was approximately 20000, while a reticulated platelet count in the blood of a healthy person is no greater than 10000.

Figure 10D:
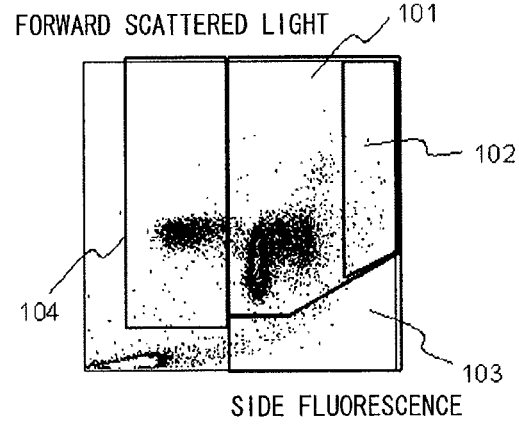

FIG. 10D is a scattergram that was obtained as a result of measuring blood collected from a patient with osteomyelodysplasia. An experiment was conducted, in which red blood cells of the blood of the patient were hemolyzed to prepare a smear and nucleated red blood cells contained in the prepared smear were visually counted. As a result, nucleated red blood cells, which are not found in the peripheral blood of a healthy person, were observed at the rate of 17 nucleated red blood cells per 1000 white blood cells.

The scattergram obtained as a result of analyzing the blood of the healthy person (FIG. 10A) was compared, using a comparison method, with the scattergrams that were obtained as a result of analyzing the blood of the respective patients whose blood was confirmed to contain abnormal blood cells (FIGS. 10B to 10D). Confirmed from this comparison was which type of abnormal blood cells appear in which position on each scattergram.

The comparison between FIG. 10A and FIG. 10B shows that few particles are present in the abnormal-WBC region 102 of FIG. 10A, whereas a substantial number of particles are present in the abnormal-WBC region 102 of FIG. 10B. The particles appearing in the abnormal-WBC region 102 in the scattergram of FIG. 10A were counted, and the particle count was 7. The particles appearing in the abnormal-WBC region 102 of FIG. 10B were also counted, and the particle count was 205. Since immature granulocytes do not appear in the peripheral blood of a healthy person, the particles appearing in the abnormal-WBC region 102 of FIG. 10B were confirmed to be immature granulocytes.

The comparison between FIG. 10A and FIG. 10C shows that few particles are present in the abnormal-PLT region 103 of FIG. 10A, whereas a substantial number of particles are present in the abnormal-PLT region 103 of FIG. 10C. The particles appearing in the abnormal-PLT region 103 in the scattergram of FIG. 10A were counted, and the particle count was 13. The particles appearing in the abnormal-PLT region 103 of FIG. 10C were also counted, and the particle count was 623. Based on the difference between these particle counts, the particles appearing in the abnormal-PLT region 103 of FIG. 10C were confirmed to be reticulated platelets.

The comparison between FIG. 10A and FIG. 10D shows that few particles are present in the abnormal-RBC region 104 of FIG. 10A, whereas a substantial number of particles are present in the abnormal-RBC region 104 of FIG. 10D. The particles appearing in the abnormal-RBC region 104 in the scattergram of FIG. 10A were counted, and the particle count was 8. The particles appearing in the abnormal-RBC region 104 of FIG. 10D were also counted, and the particle count was 1576. Since nucleated red blood cells do not appear in the blood of a healthy person, the particles appearing in the abnormal-RBC region 104 of FIG. 10D were confirmed to be nucleated red blood cells.

Accordingly, in the present embodiment, the abnormal-WBC region 102, the abnormal-PLT region 103, and the abnormal-RBC region 104 are set on the scattergram. Then, particles appearing in the abnormal-WBC region 102 are counted as the number of WBC-related abnormal blood cells contained in the sample. Moreover, particles appearing in the abnormal-PLT region 103 are counted as the number of PLT-related abnormal blood cells contained in the sample. Furthermore, particles appearing in the abnormal-RBC region 104 are counted as the number of RBC-related abnormal blood cells contained in the sample.

Return to FIG. 9. The CPU 21 of the calculation display apparatus 2 counts particles in the WBC region 101, the abnormal-WBC region 102, the abnormal-RBC region 104, and the abnormal-PLT region 103, which have been set (step S905). Results of the counting are stored in the storage device 23.

The CPU 21 determines normality/abnormality of the particle count obtained for each region (step S906). The manner of determining whether or not the obtained particle count is normal is different between the WBC region 101 and the other abnormal blood cell regions 102, 103, and 104.

Whether or not the particle count in the WBC region 101 is normal is determined based on whether or not the obtained particle count is within a numerical value range that indicates normal white blood cell counts. This is because there is a suspicion of a disease in the case where a white blood cell count in the sample is either excessively high or excessively low.

Whereas, whether or not the particle count in each of the abnormal blood cell regions 102, 103, and 104 is normal is determined based on whether or not the particle count therein is equal to or greater than a predetermined value. This is because there is a suspicion of a disease only when the count of the particles appearing therein is equal to or greater than the predetermined value, since, as described above, the particles appearing in each of the abnormal blood cell regions 102, 103, and 104 are only those related to diseases, and particles except for trash do not appear in these regions in the case of the blood of a healthy person. Note that the predetermined value is set for each of the abnormal blood cell regions 102, 103, and 104 to such a value as to eliminate the influences of contaminants, unknown particles, and the like appearing in each region.

Hereinafter, the process at step S906 will be described in detail. The CPU 21 determines whether or not the particle count in the WBC region 101 is within the predetermined numerical value range. When the CPU 21 has determined that the particle count in the WBC region 101 is within the predetermined numerical value range, the CPU 21 determines that the particle count in the WBC region 101 is normal. When the CPU 21 has determined that the particle count in the WBC region 101 is outside the predetermined numerical value range, the CPU 21 determines that the particle count in the WBC region 101 is not normal (i.e., abnormal).

Next, the CPU 21 determines whether or not the particle count in the abnormal-WBC region 102 is equal to or greater than the predetermined value. When the CPU 21 has determined that the particle count in the abnormal-WBC region 102 is less than the predetermined value, the CPU 21 determines that the particle count in the abnormal-WBC region 102 is normal. When the CPU 21 has determined that the particle count in the abnormal-WBC region 102 is equal to or greater than the predetermined value, the CPU 21 determines that the particle count in the abnormal-WBC region 102 is not normal (i.e., abnormal).

Next, the CPU 21 determines whether or not the particle count in the abnormal-PLT region 103 is equal to or greater than a predetermined value. When the CPU 21 has determined that the particle count in the abnormal-PLT region 103 is less than the predetermined value, the CPU 21 determines that the particle count in the abnormal-PLT region 103 is normal. When the CPU 21 has determined that the particle count in the abnormal-PLT region 103 is equal to or greater than the predetermined value, the CPU 21 determines that the particle count in the abnormal-PLT region 103 is not normal (i.e., abnormal).

Subsequently, the CPU 21 determines whether or not the particle count in the abnormal-RBC region 104 is equal to or greater than a predetermined value. When the CPU 21 has determined that the particle count in the abnormal-RBC region 104 is less than the predetermined value, the CPU 21 determines that the particle count in the abnormal-RBC region 104 is normal. When the CPU 21 has determined that the particle count in the abnormal-RBC region 104 is equal to or greater than the predetermined value, the CPU 21 determines that the particle count in the abnormal-RBC region 104 is not normal (i.e., abnormal).

The CPU 21 displays a result display screen on the display 25 (step S907). The result display screen includes the scattergram, which is created at step S903 and on which the regions are set at step S904, and includes measurement results on the CBC measurement items. The particle count in the WBC region, which is obtained at step S905, is displayed as a measurement result indicating a white blood cell count (WBC).

The result display screen includes a message that prompts, in accordance with a result of the determination at step S906 as to normality/abnormality of the particles, a change of the measurement mode to a different measurement mode. This process is described below.

When the CPU 21 has determined at step S906 that the white blood cell count is an abnormal value, the CPU 21 displays a message that prompts a change of the measurement mode to the DIFF mode. This is because if there is a sample of which the white blood cell count is an abnormal value, then there is a suspicion of a disease related to white blood cells and it is desired to obtain more detailed information about the white blood cells. Accordingly, a change of the measurement mode to an optimal measurement mode for the sample can be prompted, by prompting the measurement to be performed in the DIFF mode, in which the white blood cells are classified into subclasses and then measured.

When the CPU 21 has determined at step S906 that the particle count in the abnormal-WBC region is abnormal, the CPU 21 determines that presence of WBC-related abnormal blood cells has been detected, and then displays a message that prompts a change of the measurement mode to the DIFF mode. This is because if there is a sample of which the particle count in the abnormal-WBC region is equal to or greater than the predetermined value, then there is a suspicion of a disease related to white blood cells and it is desired to obtain more detailed information about the white blood cells. Accordingly, a change of the measurement mode to an optimal measurement mode for the sample can be prompted, by prompting the measurement to be performed in the DIFF mode, in which the white blood cells are classified into subclasses and then measured.

When the CPU 21 has determined at step S906 that the particle count in the abnormal-PLT region is abnormal, the CPU 21 determines that presence of PLT-related abnormal blood cells has been detected, and then displays a message that prompts a change of the measurement mode to the PLT mode. This is because if there is a sample of which the particle count in the abnormal-PLT region is equal to or greater than the predetermined value, then there is a suspicion of a disease related to platelets and it is desired to obtain more detailed information about the platelets. Accordingly, a change of the measurement mode to an optimal measurement mode for the sample can be prompted, by prompting the measurement to be performed in the PLT mode, in which the platelets are stained and then measured.

When the CPU 21 has determined at step S906 that the particle count in the abnormal-RBC region is abnormal, the CPU 21 determines that presence of RBC-related abnormal blood cells has been detected, and then displays a message that prompts a change of the measurement mode to the RET mode. This is because if there is a sample of which the particle count in the abnormal-RBC region is equal to or greater than the predetermined value, then there is a suspicion of a disease related to red blood cells and it is desired to obtain more detailed information about the red blood cells. Accordingly, a change of the measurement mode to an optimal measurement mode for the sample can be prompted, by prompting the measurement to be performed in the RET mode, in which the reticulocytes are stained and then measured.

The CPU 21 determines whether or not an instruction to change the measurement mode to a different measurement mode has been received (step S908). When the CPU 21 has determined that an instruction to change the measurement mode to a different measurement mode has not been received (step S908: NO), the CPU 21 returns the processing to step S811 of FIG. 8 to repeat the above-described processes. When the CPU 21 has determined that an instruction to change the measurement mode to a different measurement mode has been received (step S908: YES), the CPU 21 transmits, to the measurement apparatus 1, an instruction signal that provides an instruction to change the measurement mode (step S909). Then, the CPU 21 returns the processing to step S817 of FIG. 8 to repeat the above-described processes.

When the CPU 21 has determined at step S901 that the measurement mode is not the CBC mode (step S901: NO), the CPU 21 performs a process corresponding to the measurement mode (step S910). Then, the CPU 21 returns the processing to step S811 of FIG. 8 to repeat the above-described processes. The process corresponding to the measurement mode is described below.

For example, when the measurement mode is the DIFF mode, generation of distribution data and creation of a scattergram are performed in the same manner as that of steps S902 and S903. On the scattergram, regions in each of which white blood cells of a corresponding subclass appear (here, the subclasses of white blood cells are neutrophils, eosinophils, basophile, monocytes, and lymphocytes) are set (i.e., gating). Particles appearing in each region are counted. The results of the counting are displayed on the display 25 as count values of the subclasses of white blood cells.

Whereas, when the measurement mode is the RET mode, generation of distribution data and creation of a scattergram are performed in the same manner as that of steps S902 and S903. On the scattergram, a region in which reticulocytes appear is set (i.e., gating). Particles in the region are counted. The result of the counting is displayed on the display 25 as a count value of the reticulocytes.

Further, when the measurement mode is the PLT mode, generation of distribution data and creation of a scattergram are performed in the same manner as that of steps S902 and S903. On the scattergram, a region in which platelets appear is set (i.e., gating). Particles in the region are counted. The result of the counting is displayed on the display 25 as a count value of the platelets.

Return to FIG. 8. The CPU 21 of the calculation display apparatus 2 determines whether or not a shutdown instruction has been received (step S811). When the CPU 21 has determined that a shutdown instruction has not been received (step S811: NO), the CPU 21 returns the processing to step S803 to repeat the above-described processes. When the CPU 21 has determined that a shutdown instruction has been received (step S811: YES), the CPU 21 transmits shutdown instruction information to the measurement apparatus 1 (step S812).

The controller 91 of the control board 9 of the measurement apparatus 1 determines whether or not the shutdown instruction information has been received (step S821). When the controller 91 has determined that the shutdown instruction information has not been received (step S821: NO), the controller 91 returns the processing to step S814 to repeat the above-described processes. When the controller 91 has determined that the shutdown instruction information has been received (step S821: YES), the controller 91 performs a shutdown (step S822) to end the processing.

Figure 11:
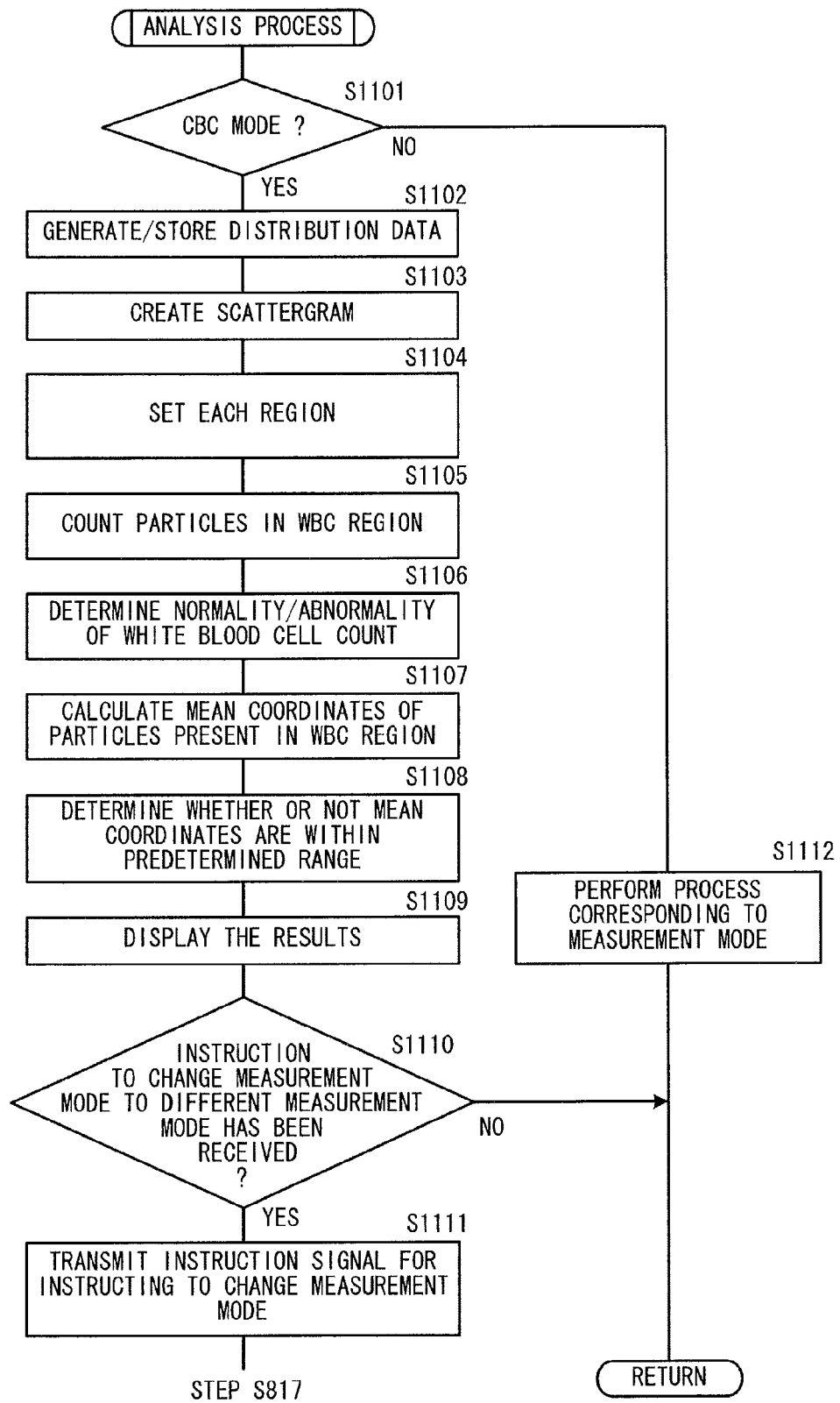
FIG. 11 is a flowchart showing steps of an analysis process that is performed, based on mean coordinates in the WBC region, by the CPU of the calculation display apparatus according to the embodiment of the present invention.

The above-described embodiment gives an example where the regions in which abnormal blood cells appear are set, and particles appearing in each set region are counted to determine presence or absence of abnormal blood cells therein. Note that, as an alternative, presence or absence of abnormal blood cells can be determined based on mean coordinates of particles appearing in a region in which white blood cells are distributed. FIG. 11 is a flowchart showing steps of the analysis process that is performed, based on mean coordinates in the WBC region, at step S810 in FIG. 8 by the CPU 21 of the calculation display apparatus 2 according to the embodiment of the present invention.

In FIG. 11, based on the received measurement data, the CPU 21 of the calculation display apparatus 2 reads, from the storage device 23, the measurement mode, in which the sample measurement has been performed and thereby the measurement data has been obtained, and the CPU 21 determines whether or not the measurement mode is the CBC mode (step S1101).

When the CPU 21 has determined that the measurement mode is the CBC mode (step S1101: YES), the CPU 21 generates, for each particle contained in the sample, distribution data that contains two parameters which have been obtained for said each particle, the two parameters representing the forward scattered light intensity and the side fluorescence intensity. The CPU 21 associates the generated distribution data with subject information, and stores the distribution data in the distribution data storage section 231 of the storage device 23 (step S1102). The CPU 21 creates a scattergram as shown in FIG. 7, on which the distribution data is plotted based on the forward scattered light intensity and the side fluorescence intensity (step S1103).

The CPU 21 sets, on the scattergram, a WBC region for counting white blood cells, an abnormal-WBC region for detecting WBC-related abnormal blood cells, an abnormal-RBC region for detecting nucleated red blood cells, and an abnormal-PLT region for detecting PLT-related abnormal blood cells (i.e., gating) (step S1104).

The CPU 21 counts particles in the set WBC region (a white blood cell count) (step S1105). The CPU 21 determines whether or not the white blood cell count obtained at step S1105 is normal (step S1106). Since the manner of determining whether or not the white blood cell count is normal is the same as that of the above-described step S906 of FIG. 9, the detailed description thereof is omitted.

The CPU 21 calculates the mean coordinates of the particles present in the WBC region (step S1107). That is, the CPU 21 calculates the mean value of the side fluorescence intensity (i.e., the mean value of the X-coordinates) of the particles present in the WBC region, and the mean value of the forward scattered light intensity (i.e., the mean value of the Y-coordinates) of the particles present in the WBC region. The side fluorescence intensity and the forward scattered light intensity tend to increase in accordance with an increase in the amount of abnormal blood cells such as immature granulocytes. Accordingly, when there is an increase in the amount of such abnormal blood cells, the mean coordinates of the particles present in the WBC region shift toward the upper right of the scattergram. Therefore, abnormal blood cells can be detected by determining whether or not the shift amount is within a predetermined range.

The CPU 21 determines whether or not the calculated mean coordinates are within a predetermined range (step S1108), and displays a result display screen on the display 25 (step S1109). Since the contents of the result display screen are the same as those displayed at the above-described step S907 of FIG. 9, the detailed description thereof is omitted.

The result display screen includes a message that prompts the measurement to be performed in a different measurement mode in accordance with a result of the determination at step S1106 as to normality/abnormality of the white blood cell count and a result of the determination at step S1108 as to whether or not the mean coordinates are within the predetermined range.

When the CPU 21 has determined at step S1106 that the white blood cell count is an abnormal value, or determined at step S1108 that the mean coordinates are outside the predetermined range, the CPU 21 displays a message that prompts the measurement to be performed in the DIFF mode. This is because either in the case where the white blood cell count is an abnormal value or in the case where the mean coordinates of the particles in the WBC region have shifted due to the appearance of abnormal blood cells such as immature granulocytes, there is a suspicion of a disease related to white blood cells and it is desired to obtain more detailed information about the white blood cells. Accordingly, when the white blood cell count is an abnormal value, or when the mean coordinates of the particles present in the WBC region are outside the predetermined range, a change of the measurement mode to an optimal measurement mode for the sample can be prompted, by prompting the measurement to be performed in the DIFF mode, in which the white blood cells are classified into subclasses and then measured.

The CPU 21 determines whether or not an instruction to change the measurement mode to a different measurement mode has been received (step S1110). When the CPU 21 has determined that an instruction to change the measurement mode to a different measurement mode has not been received (step S1110: NO), the CPU 21 returns the processing to step S811 of FIG. 8 to repeat the above-described processes. When the CPU 21 has determined that an instruction to change the measurement mode to a different measurement mode has been received (step S1110: YES), the CPU 21 transmits, to the measurement apparatus 1, an instruction signal that provides an instruction to change the measurement mode (step S1111). Then, the CPU 21 returns the processing to step S817 of FIG. 8 to repeat the above-described processes. When the CPU 21 has determined at step S1101 that the measurement mode is not the CBC mode (step S1101: NO), the CPU 21 performs a process corresponding to the measurement mode (step S1112). Then, the CPU 21 returns the processing to step S811 of FIG. 8 to repeat the above-described processes. Since the process corresponding to the measurement mode is the same as the process described above with reference to FIG. 9, the detailed description thereof is omitted.

As described above, according to the present embodiment, abnormal blood cells can be detected based on the distribution data that is obtained from the measurement in the CBC mode of which the reagent cost is relatively low. Accordingly, the entire measurement cost including the reagent cost can be kept low. Further, a change of the measurement mode to the DIFF mode, the RET mode, or the PLT mode, each of which enables the measurement of more detailed measurement items, can be prompted.

Further, as shown in the flowcharts of FIGS. 9 and 11, a message for prompting a change of the measurement mode can be displayed not only in the case where abnormal blood cells have been detected but also in the case where the white blood cell count is an abnormal value. Accordingly, a user can be informed not only about abnormality of a sample, which is due to the appearance of abnormal blood cells, but also about abnormality of a white blood cell count, which is not due to the appearance of abnormal blood cells.

In the above-described embodiment, the analysis results are displayed on the display 25 of the calculation display apparatus 2. However, the present invention is not particularly limited thereto. Alternatively, the analysis results may be displayed on a display of a different computer that is connected to the calculation display apparatus 2 via a network. Further alternatively, the measurement apparatus 1 may be provided with a display such as an LCD that is capable of displaying the analysis results.

Although the abnormal-WBC region and the abnormal-PLT region are separately set on the scattergram in the above-described embodiment, the manner of setting a region for detecting presence of abnormal blood cells is not limited thereto. For example, it is understood that a single region for detecting presence of abnormal blood cells may be set on the scattergram, regardless of the difference between WBC-related abnormal blood cells and PLT-related abnormal blood cells.

The above embodiment describes, as an example, the blood analyzer that is configured to be able to receive the selection of a measurement mode that is selected from among the CBC mode and the other measurement modes. However, the present invention is not limited thereto. For example, the blood analyzer may be configured to measure only the CBC measurement items. Here, the blood analyzer may be configured to perform, for all samples, measurement of the CBC measurement items and detection of abnormal blood cells. In this case, a blood analysis system may be constructed, which includes, for example, a first blood analyzer for measuring only the CBC measurement items and a second blood analyzer for measuring measurement items different from the CBC measurement items. This blood analysis system may be configured such that when the first blood analyzer has detected abnormal blood cells, the second blood analyzer measures the measurement items different from the CBC measurement items.

The present invention is not limited to the above-described embodiment. It is understood that various modifications, replacements, and the like can be devised without departing from the spirit and scope of the present invention.

What is claimed is:

1. A blood analyzer comprising:

a specimen preparation section comprising a reaction chamber configured to prepare, by using a staining reagent and a blood sample obtained from a subject, a measurement specimen to be tested for CBC measurement items under a CBC measurement mode that include a white blood cell count;

a measurement section comprising a flow cell through which a flow of the measurement specimen runs, a light emitter operable to irradiate the flow flowing in the flow cell, a first light receiver operable to receive a forward scattered light from the measurement specimen and a second light receiver operable to receive a fluorescence light emitted from the measurement specimen, the measurement section configured to obtain a forward scattered light intensity and a fluorescence light intensity for a respective particles in the measurement specimen; and a controller including a memory, the memory storing instructions programming the controller to:

plot the respective particles on a CBC scattergram at a location addressed by the forward scattered light intensity and fluorescence light intensity obtained for the respective particles, the CBC scattergram being a two-dimensional coordinate plane defined by mutually orthogonal coordinates representing the forward scattered light intensity and the fluorescent light intensity, and the CBC scattergram having a WBC region defined in the CBC scattergram to encompass normal white blood cells plotted on the CBC scattergram and an abnormal PLT region defined in the CBC scattergram separately and independently from the WBC region to encompass a majority of abnormal platelets plotted on the CBC scattergram;

count a number of plotted particles in the WBC region to derive a white blood cell count;

count a number of plotted particles in the abnormal PLT region; and if the number of plotted particles counted in the abnormal PLT region exceeds a predetermined abnormal PLT threshold value, output a message, under the CBC measurement mode, notifying that the blood sample may contain abnormal platelets, wherein the staining reagent contains a fluorescent dye selected from the group consisting of a fluorescent dye represented by the general formula (I):

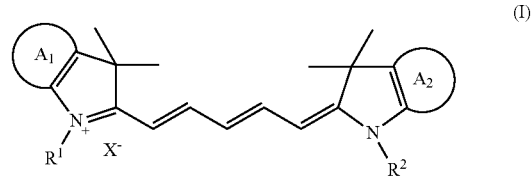

(I)

wherein $R^1$ and $R^2$ are identical to or different from each other, an alkyl group;

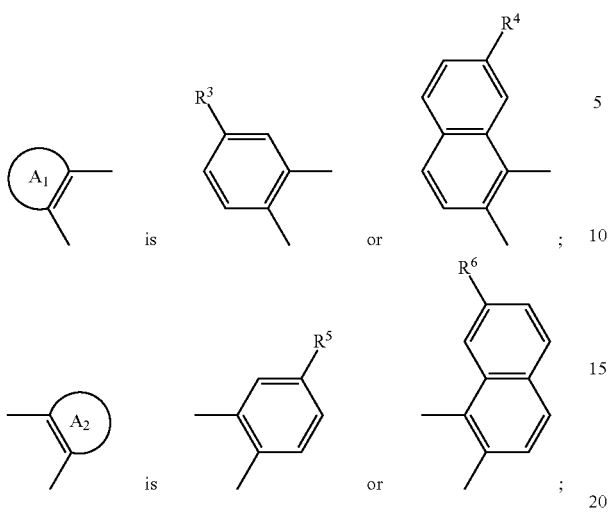

$R^3$, $R^4$, $R^5$ and $R^6$ are identical to or different from each other, a hydrogen atom or an alkyl group; and $X^-$ is an anion; and a fluorescent dye represented by the general formula (II):

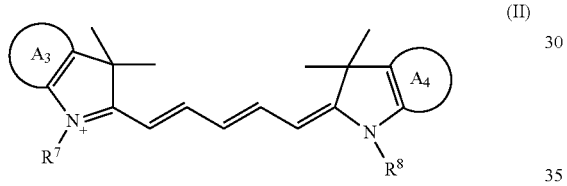

wherein $R^7$ and $R^8$ are identical to or different from each other, an alkyl group that may have an acid group;

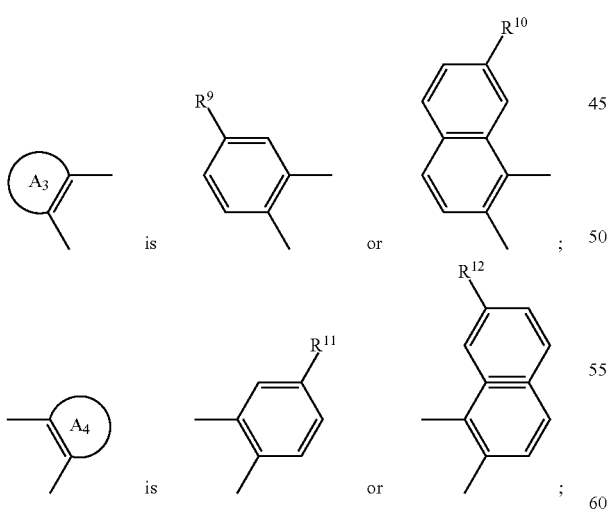

$R^9$, $R^{10}$, $R^{11}$ and $R^{12}$ are identical to or different from each other, a hydrogen atom or an acid group that exists in at least one of $R^7$ to $R^{12}$, the acid group that may exist $R^7$ to $R^{12}$ may form a salt, at least one of the acid groups that may exist $R^7$ to $R^{12}$ is a group from which a proton has been released.

2. The blood analyzer of claim 1, further comprising a display for displaying the scattergram.

3. The blood analyzer of claim 1, wherein the controller is programmed to receive a selection of one measurement mode selected from a plurality of measurement modes, the plurality of measurement modes comprising:
the CBC measurement mode for measuring the CBC measurement items that include at least a white blood cell count, a red blood cell count, and a platelet count; and
at least one other measurement mode for measuring a measurement item not included in the CBC measurement items.

4. The blood analyzer of claim 3, wherein
the at least one other measurement mode comprises a platelet measurement mode for obtaining information about platelets, and
the controller is programmed to output a message, under the CBC measurement mode, which prompts a user to test the blood sample under the platelet measurement mode when the number of plotted particles counted in the abnormal PLT region exceeds the predetermined abnormal PLT threshold value.

5. The blood analyzer of claim 1 wherein,
the CBC scattergram further has an abnormal RBC region defined in the CBC scattergram separately and independently from the WBC region and the abnormal PTL region to encompass abnormal red blood cells plotted on the CBC scattergram,
the controller is programmed to count a number of plotted particles in the abnormal RBC region and, if the number of plotted particles counted in the abnormal RBC region exceeds a predetermined abnormal RBC threshold value, output a message, under the CBC measurement mode, notifying that the blood sample may contain nucleated red blood cells.

6. The blood analyzer of claim 5, wherein the controller is programmed to receive a selection of one measurement mode selected from a plurality of measurement modes,
the plurality of measurement modes comprising:
the CBC measurement mode for measuring the CBC measurement items that include at least a white blood cell count, a red blood cell count and a platelet count; and
a RET mode for obtaining information about red blood cells, and
the controller is programmed to output a message, under the CBC measurement mode, which prompts a user to test the blood sample under the RET mode when the number of plotted particles counted in the abnormal RBC region exceeds the predetermined RBC threshold value.

7. The blood analyzer of claim 1 wherein
the CBC scattergram further has an abnormal WBC region defined in the CBC scattergram separately and independently from the WBC region and the abnormal PTL region to encompass abnormal white blood cells plotted on the CBC scattergram, and
the controller is programmed to count a number of plotted particles in the abnormal WBC region and, if the number of plotted particles counted in the abnormal WBC region exceeds a predetermined abnormal WBC threshold value, output a message, under the CBC measurement mode, notifying that the blood sample may contain immature granulocyte.

8. The blood analyzer of claim 7, wherein the controller is programmed to receive a selection of one measurement mode selected from a plurality of measurement modes, the plurality of measurement modes comprising:
the CBC measurement mode for measuring the CBC measurement items that include at least a white blood cell count, a red blood cell count and a platelet count: and
a DIFF mode for obtaining information about white blood cells, and the controller is programmed to output a message, under the CBC measurement mode, which prompts a user to test the blood sample under the DIFF mode when the number of plotted particles counted in the abnormal WBC region exceeds the predetermined abnormal WBC threshold value.

9. The blood analyzer of claim 8, wherein the controller is programmed to output a message, under the CBC measurement mode, prompts to test the blood sample under the DIFF mode when the number of plotted particles counted in the WBC region is not within a predetermined value range.

10. The blood analyzer of claim 1, wherein the second light receiver is an avalanche photodiode.

11. The blood analyzer of claim 1, wherein the measurement sample is prepared by further using hemolytic agent.

12. The blood analyzer of claim 1, wherein the controller is programmed to receive a selection of mode from a group including at least the CBC measurement mode for measuring the CBC measurement items and a DIFF mode for measuring numbers of subclasses of white blood cells, and the fluorescent dye used to measure the white blood cell count of the CBC measurement items is different from a fluorescent dye used in the DIFF mode.

13. The blood analyzer of claim 1, wherein the specimen preparation section includes a first chamber for preparing the measurement specimen used to measure the white blood cell count under the CBC measurement mode and a second chamber for preparing a second measurement specimen used to measure a number of red blood cells and a number of platelets under the CBC measurement mode, the first chamber is connected to the flow cell, and
the second chamber is connected to an electrical detector.

14. The blood analyzer of claim 1, further comprising a pipette for aspirating a blood sample from a blood collection tube.

15. The blood analyzer of claim 1, wherein the fluorescent dye is selected from the group consisting of NK-529, NK-2670, NK-3750, NK-3383, NK-1840, NK-9001, NK-9003, NK-2929, NK-3375, NK-5056, NK-3266 and NK-3620.

* * * * *